United States Patent
Yokota et al.

(10) Patent No.: US 7,032,436 B2
(45) Date of Patent: Apr. 25, 2006

(54) METHOD FOR ESTIMATING VEHICULAR RUNNING STATE, VEHICULAR RUNNING STATE ESTIMATING DEVICE, VEHICLE CONTROL DEVICE, AND TIRE WHEEL

(75) Inventors: Hidetoshi Yokota, Tokyo (JP); Hiroshi Morinaga, Tokyo (JP); Koji Otani, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 0 days.

(21) Appl. No.: 10/049,509

(22) PCT Filed: Jun. 21, 2001

(86) PCT No.: PCT/JP01/05298

§ 371 (c)(1),
(2), (4) Date: Jun. 7, 2002

(87) PCT Pub. No.: WO01/98123

PCT Pub. Date: Dec. 27, 2001

(65) Prior Publication Data

US 2002/0162389 A1    Nov. 7, 2002

(30) Foreign Application Priority Data

Jun. 23, 2000  (JP) ............................. 2000-190231

(51) Int. Cl.
*G01B 5/28* (2006.01)
(52) U.S. Cl. .................... 73/105; 73/11.04; 73/118.1
(58) Field of Classification Search .............. 73/105, 73/7, 8, 9, 11.04, 11.05, 11.07, 11.08, 11.09, 73/104, 118.1
See application file for complete search history.

(56) References Cited

U.S. PATENT DOCUMENTS

| | | | | | |
|---|---|---|---|---|---|
| 4,658,656 A | * | 4/1987 | Haeg | ............................. | 73/669 |
| 4,837,727 A | * | 6/1989 | Tashiro et al. | .............. | 702/167 |
| 4,984,163 A | * | 1/1991 | Kuwana et al. | ................ | 701/80 |
| 5,034,890 A | * | 7/1991 | Sugasawa et al. | ............ | 701/37 |
| 5,065,618 A | * | 11/1991 | Hodges et al. | ................ | 73/146 |
| 5,075,855 A | * | 12/1991 | Sugasawa et al. | ............ | 701/37 |
| 5,222,570 A | * | 6/1993 | Kawamura et al. | ......... | 180/197 |
| 5,355,717 A | * | 10/1994 | Tanaka et al. | ................ | 73/105 |

(Continued)

FOREIGN PATENT DOCUMENTS

EP    0 421 065 A2    4/1991

(Continued)

*Primary Examiner*—Eric S. McCall
(74) *Attorney, Agent, or Firm*—Sughrue Mion, PLLC

(57) ABSTRACT

The output level of vibration of a portion below the spring of a vehicle detected by a sensor, and its frequency is converted to obtain the frequency spectrum of the vibration level. Next, an operation is carried out on at least two vibration levels, at different frequency bands. The computed value is compared with a master curve showing the frequency spectrum of vibration level stored in vibration level storage to estimate the condition of a road surface so as to estimate the running state of the vehicle. Further, the running state of each tire including air pressure is detected from the vibration level of the portion below the spring to estimate the running state of the vehicle. Thereby, a multi-function sensing system is constructed for estimating the condition of a road surface or the running state of the tire with one sensor.

33 Claims, 18 Drawing Sheets

U.S. PATENT DOCUMENTS

| | | | | |
|---|---|---|---|---|
| 5,723,768 | A | * | 3/1998 | Ammon .......................... 73/8 |
| 5,749,984 | A | | 5/1998 | Frey et al. |
| 5,878,365 | A | | 3/1999 | Onogi et al. |
| 6,046,672 | A | | 4/2000 | Pearman |
| 6,640,623 | B1 | * | 11/2003 | Ono et al. .................... 73/146 |
| 2002/0013652 | A1 | * | 1/2002 | Yasui et al. ................... 701/80 |
| 2002/0059824 | A1 | * | 5/2002 | Ono et al. .................... 73/146 |
| 2003/0218379 | A1 | * | 11/2003 | Miyazaki ................... 303/150 |
| 2004/0015312 | A1 | * | 1/2004 | Asano et al. ............... 702/113 |
| 2004/0064219 | A1 | * | 4/2004 | Mancosu et al. .............. 701/1 |

FOREIGN PATENT DOCUMENTS

| | | |
|---|---|---|
| EP | 0 783 982 A1 | 7/1997 |
| EP | 0 795 448 A2 | 9/1997 |
| EP | 0 891 904 A2 | 1/1999 |

* cited by examiner

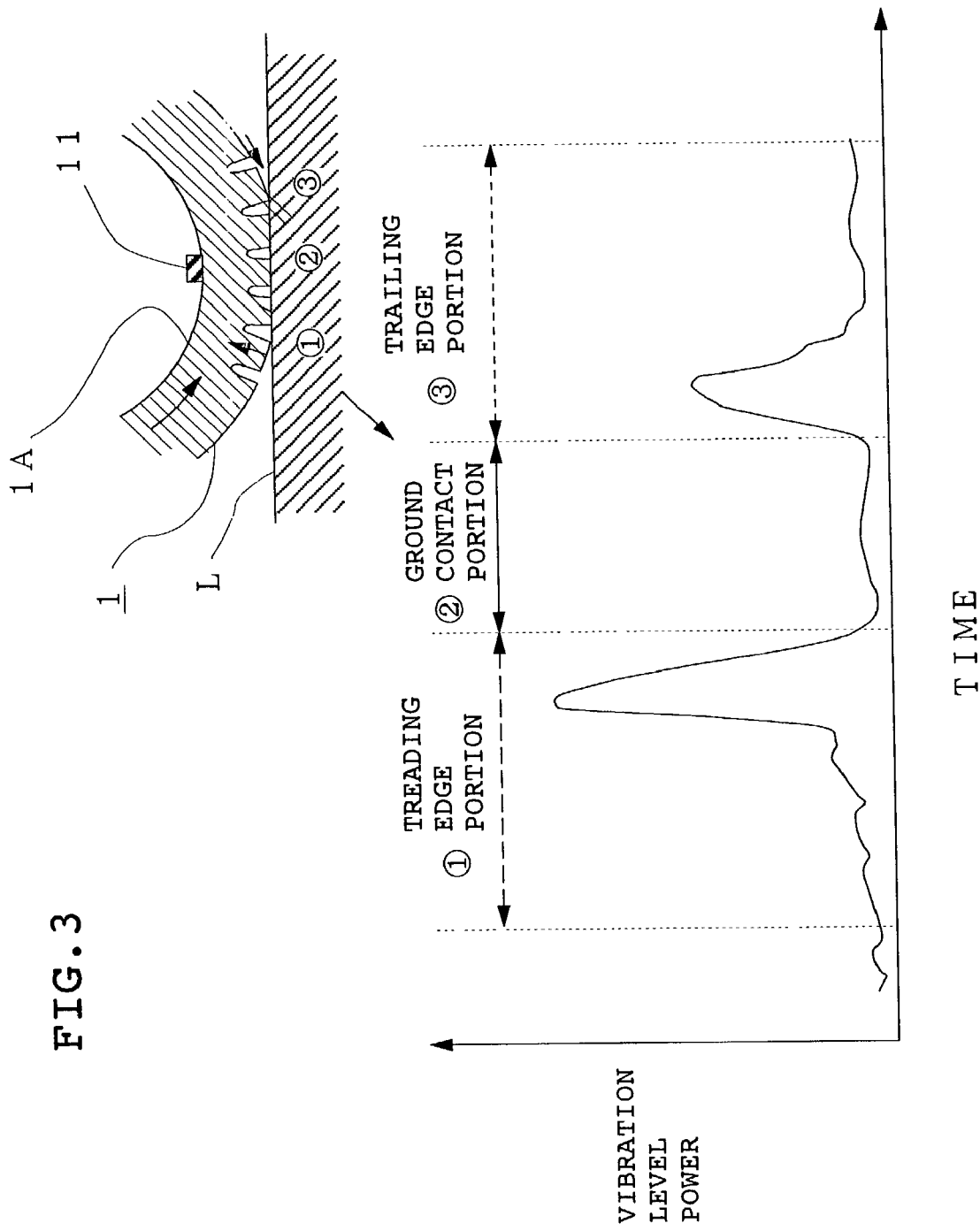

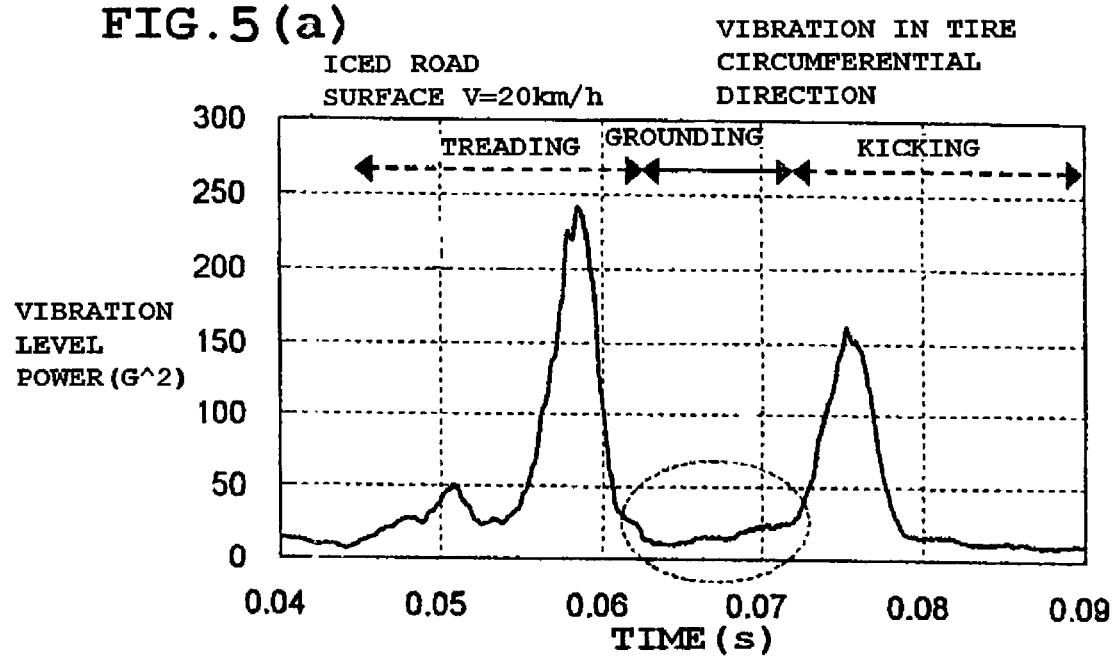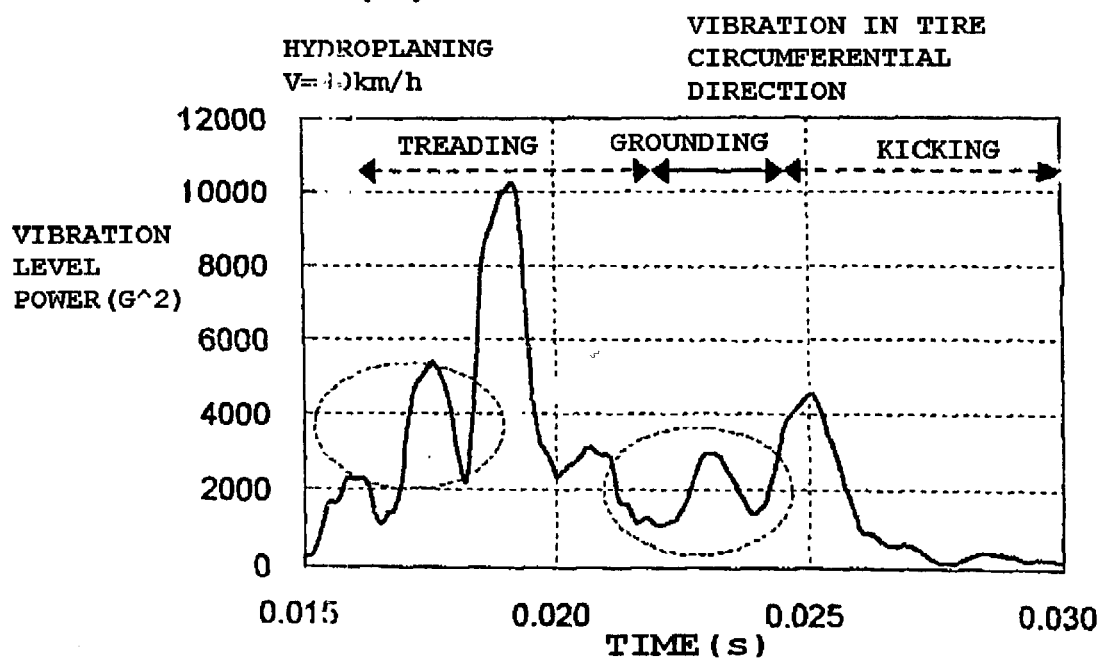

METHOD FOR ESTIMATING VEHICULAR RUNNING STATE, VEHICULAR RUNNING STATE ESTIMATING DEVICE, VEHICLE CONTROL DEVICE, AND TIRE WHEEL

BACKGROUND OF THE INVENTION

1. Field of the Invention

The present invention relates to a method and apparatus for estimating the running state of a vehicle by estimating the condition of a road surface or the running state of each tire while running, an apparatus for controlling a vehicle based on the estimated running state of a vehicle, and a tire wheel comprising the above vehicle running state estimation apparatus and a power generating unit for activating this apparatus.

2. Description of the Prior Art

In recent years, it has been desired that the relationship between each tire and the surface of a road which is the most important factor for the safe running of a vehicle, specifically, the ground contact state of the tire typified by a friction coefficient between the tire and the surface of a road (road surface friction coefficient) or the condition of a road surface, or the running state of the tire such as the distortion and air pressure of the tire should be estimated with high accuracy and fedback to vehicle control. That is, if the above ground contact state and running state of the tire can be estimated in advance, before the operation of avoiding a risk such as braking or steering is taken, high-level control of an ABS brake will be made possible and further improvement of safety will be expected. The driver can carry out deceleration operation earlier if he is informed of the risk of the condition of a road surface while running, whereby a reduction in the number of accidents can be expected.

To estimate a road surface friction coefficient, there are proposed a method of estimating a road surface friction coefficient making use of the fact that the uniformity level of each tire which is a physical quantity indicative of a change in the revolution speed of each wheel is changed by the size of a road surface friction coefficient (Japanese Laid-open Patent Application No. 2000-55790) and a method of estimating a road surface friction coefficient making use of the fact that the horizontal-direction vibration of each tire having a toe angle is detected by attaching an accelerometer to a lower arm for connecting the front wheels and the vehicle body and this vibration level is changed by a road surface friction coefficient (Japanese Laid-open Patent Application No. 6-258196).

However, in the above method of estimating a road surface friction coefficient from the uniformity level of the tire, the uniformity is deteriorated by the formation of a flat spot in the tire and in the course of recovery from this, accurate estimation is difficult.

Meanwhile, in the above method of estimating a road surface friction coefficient from the horizontal-direction vibration of the front wheels having a toe angle, the measurement accuracy is low when the slip angle of the tire is taken completely null or large.

There is also proposed a method of estimating a road surface friction coefficient from transmission characteristics between acceleration below a spring which is acceleration in the vertical direction of each wheel and acceleration above the spring which is acceleration in the vertical direction of the vehicle body (Japanese Laid-open Patent Application No. 11-94661). This method has such an advantage that the road surface friction coefficient on a straight road for which almost no steering action is carried out can be estimated because steering force is not used for the estimation of a road surface friction coefficient. However, as the road surface friction coefficient is estimated from vibration transmission characteristics between two points through a suspension unit having large buffer characteristics such as a spring or damper, the road surface friction coefficient is readily affected by the uneven surface of the road. For instance, as vibration under a spring is large on a rough road such as a road covered with snow, the difference in vibration level between vibration above the spring absorbed by a suspension and vibration below the spring becomes large, thereby making it impossible to estimate a road surface friction coefficient accurately.

Meanwhile, the internal pressure of the tire is also an important factor for the running condition of the tire. Stated more specifically, the ground contact state of the tire and the running state of the tire are accurately estimated from the distortion state or vibration level of the tire while rolling and grip performance is improved or riding comfort is improved by increasing the ground contact area or rigidity of the tire is reduced to reduce the internal pressure of the tire when the grip performance of the tire is reduced on a wet road or road covered with iced snow or when the vehicle runs on a rough road. Conversely when the vehicle runs at a high speed or a hydroplaning phenomenon occurs, the running fuel cost must be improved or the recovery of steerability must be promoted by increasing the internal pressure of the tire.

However, since a sensor, which is ground contact state detection means for measuring the distortion state or vibration level of the tire while rolling, requires a electric power source, the power must be supplied to the above sensor. Further, when an apparatus for estimating or controlling the condition of a road surface or the running state of the tire based on the output of the above ground contact state detection means and a radio unit for transmitting an output signal from road surface condition estimation means or the like to the vehicle body are mounted to the tire, a electric power supply to the above apparatus and radio unit is necessary.

For the power supply to the tire as a rotor, electromotive force is transferred through a slip ring or generated by electromagnetic induction making use of relative movement between vehicle body and the tire may be used. However, the structure of the vehicle body must be changed for means of supplying power to these, thus boosting costs.

Although it can be said that it is the most realistic method to load batteries which are to be exchanged, there remain such problems as the troublesome exchange and service life of the batteries.

The development of a system which estimates the running state of a vehicle such as the condition of a road surface or the running state of each tire accurately, supplies information on the running state of the vehicle to the vehicle and the driver and controls the characteristics of the tire using the above information to provide a more safe or more comfortable running state has been desired.

It is an object of the present invention which has been made in view of the above problems of the prior art to provide a method and apparatus for estimating the running state of a vehicle such as the condition of a road surface or the running state of each tire while running accurately, a vehicle control apparatus for improving the safety of a vehicle by feedback controlling the running state of the vehicle based on the estimated condition of a road surface or the estimated running state of each tire, and a tire wheel comprising the above vehicle running state estimation apparatus and a power generating unit for activating the apparatus.

SUMMARY OF THE INVENTION

To attain the above object, the inventor of the present invention has conducted various studies and has found that the running state of a vehicle such as the condition of a road surface or the running state of each tire while running is estimated by detecting the vibration level of a portion below the spring of a running vehicle or the vibration transmission level between at least two points of a portion below the spring of the vehicle, thereby making it possible to estimate the running state of the vehicle accurately even when the road is rough, which has been difficult with the prior art, or when the slip angle is null. The present invention has been accomplished based on this finding.

That is, according to a first aspect of the present invention, there is provided a vehicle running state estimation method comprising the steps of detecting the vibration level of a portion below the spring of a running vehicle, and estimating at least one of the condition of a road surface on which the vehicle is running and the running state of each tire based on the above detected vibration level to estimate the running state of the vehicle. Generally the portion below the spring of the vehicle means a suspension, hub, brake caliper, wheel, and tire. In the case of having no spring in the suspension such as hydraulic unit the portion means on the tire side from the unit.

According to a second aspect of the present invention, there is provided a vehicle running state estimation method, wherein the waveform of time changes in the above vibration level is detected and the condition of a road surface on which the vehicle is running is estimated from a vibration level at a predetermined position of this waveform or for a predetermined time range.

According to a third aspect of the present invention, there is provided a vehicle running state estimation method, wherein the frequency of the above detected vibration level is analyzed a vibration level at a predetermined frequency band and the condition of a road surface on which the vehicle is running is estimated from the above calculated vibration level.

According to a fourth aspect of the present invention, there is provided a vehicle running state estimation method, wherein the frequency of the above detected vibration level is analyzed, at least two vibration levels at different frequency bands are calculated, an operation is carried out on the above calculated vibration levels, and the condition of a road surface on which the vehicle is running is estimated from the operated value.

According to a fifth aspect of the present invention, there is provided a vehicle running state estimation method, wherein the vibration levels of at least two points of a portion below the spring of a running vehicle are detected to calculate the vibration transmission level of the portion below the spring of the vehicle, and the condition of a road surface on which the vehicle is running is estimated from the above calculated vibration transmission level.

According to a sixth aspect of the present invention, there is provided a vehicle running state estimation apparatus comprising:

means of detecting the vibration level of a portion below the spring of a running vehicle;

means of computing the waveform of time changes in the above vibration level; and road surface condition estimation means for estimating the condition of a road surface on which the vehicle is running from a vibration level at a predetermined position of the above waveform or for a predetermined time range.

According to a seventh aspect of the present invention, there is provided a vehicle running state estimation apparatus which further comprises means of calculating the vibration level of at least one of a tire leading edge portion, tire ground contact portion and tire trailing edge portion of the above waveform.

According to an eighth aspect of the present invention, there is provided a vehicle running state estimation apparatus comprising:

means of detecting the vibration level of a portion below the spring of a running vehicle;

means of calculating a vibration level at a predetermined frequency band by analyzing the frequency of the above detected vibration level; and road surface condition estimation means for estimating the condition of a road surface on which the vehicle is running from the above calculated vibration level.

According to a ninth aspect of the present invention, there is provided a vehicle running state estimation apparatus comprising:

means of detecting the vibration level of a portion below the spring of a running vehicle; and road surface condition estimation means for estimating the condition of a road surface on which the vehicle is running from a value obtained by carrying out an operation on at least two vibration levels at different frequency bands by analyzing the frequency of the above detected vibration level.

According to a tenth aspect of the present invention, there is provided a vehicle running state estimation apparatus comprising:

means of detecting the vibration levels of at least two points of a portion below the spring of a running vehicle;

means of calculating a vibration transmission level at a predetermined frequency band between the at least two of the above vibration detection points; and road surface condition estimation means for estimating the condition of a road surface on which the vehicle is running from the above calculated vibration transmission level.

According to an eleventh aspect of the present invention, there is provided a vehicle running state estimation apparatus, wherein a vibration buffer member is interposed between the above at least two vibration detection points.

According to a twelfth aspect of the present invention, there is provided a vehicle running state estimation apparatus, wherein the relationship between road surface friction coefficient µ obtained from the braking distances of a vehicle under various road conditions at different speeds and the above vibration level at a predetermined frequency band, the computed value of vibration level or vibration transmission level is obtained previously and the road surface friction coefficient µ at the time of running is estimated based on the above relationship.

According to a thirteenth aspect of the present invention, there is provided a vehicle running state estimation apparatus, wherein the above frequency band is a band including the frequency of natural vibration of a tire tread land portion.

According to a fourteenth aspect of the present invention, there is provided a vehicle running state estimation apparatus, wherein a threshold value is set for the above vibration level and the surface of a road is estimated to be in a low friction condition when the calculated vibration level exceeds the above threshold value.

According to a fifteenth aspect of the present invention, there is provided a vehicle running state estimation apparatus, wherein the above threshold value can be changed.

According to a sixteenth aspect of the present invention, there is provided a vehicle running state estimation apparatus which further comprises vehicle speed detection means to estimate the condition of a road surface based on vehicle speed.

According to a seventeenth aspect of the present invention, there is provided a vehicle running state estimation apparatus comprising the vehicle running state estimation apparatus of any one of claims 6 to 16, means of judging the slipperiness of a road surface based on the condition of the road surface estimated by the road surface condition estimation means of the vehicle running state estimation apparatus and warning means for giving a warning when it is judged that the condition of the road surface is slippery.

According to an eighteenth aspect of the present invention, there is provided a vehicle running state estimation apparatus which further comprises vehicle speed detection means to change decision on the slipperiness of a road surface and warning level based on vehicle speed.

According to a nineteenth aspect of the present invention, there is provided a vehicle running state estimation apparatus comprising:

means of detecting the vibration level of a portion below the spring of a running vehicle;

means of estimating the air pressure of each tire by calculating the frequency of natural vibration of the tire from a vibration level at a frequency band of 200 Hz or less of the above detected vibration level; and tire running state estimation means for estimating the condition of each tire while running from the above estimated air pressure of the tire.

According to a twentieth aspect of the present invention, there is provided a vehicle running state estimation apparatus which further comprises tire pressure monitoring means for monitoring the pressure of each tire while running using the above estimated air pressure of the tire.

According to a twenty-first aspect of the present invention, there is provided a vehicle running state estimation apparatus which further comprises warning means for warning a passenger of a reduction in the pressure of the tire when the air pressure monitored by the above tire pressure monitoring means falls below a predetermined value.

According to a twenty-second aspect of the present invention, there is provided a vehicle running state estimation apparatus comprising:

means of detecting the vibration level of a portion below the spring of a running vehicle;

tire revolution speed detection means;

tire running state estimation means for estimating the state of each tire while running by calculating the average value of vibration level changing by the revolution speed of the tire at a frequency band of 100 Hz or less of the above detected vibration level; and tire trouble detection means for judging that the tire is abnormal when the above calculated average value of vibration level exceeds a preset reference value.

According to a twenty-third aspect of the present invention, there is provided a vehicle running state estimation apparatus, wherein the above reference value is set to a range of 1.2 to 5 times the vibration level at a reference decision frequency Fn when the vehicle runs at a predetermined speed V while the tire is not abnormal:

reference decision frequency $Fn = n \times V/(2\pi r)$ wherein r is the rolling radius of the tire, and n is 1, 2, 3, . . . .

According to a twenty-fourth aspect of the present invention, there is provided a vehicle running state estimation apparatus, wherein the above reference value can be changed.

According to a twenty-fifth aspect of the present invention, there is provided a vehicle running state estimation apparatus which further comprises a transmitter for transmitting the output of the above vibration detection means for calculating a time change in vibration level or a vibration level at a predetermined frequency band.

According to a twenty-sixth aspect of the present invention, there is provided a vehicle running state estimation apparatus further comprising a electric power generating unit which is mounted to a tire wheel, generates power by the rolling of each tire and supplies power for driving the above vibration detection means or power for amplifying the output of the above vibration detection means.

According to a twenty-seventh aspect of the present invention, there is provided a vehicle control apparatus comprising vehicle control means for controlling the running state of a vehicle based on the condition of a road surface estimated by the vehicle running state estimation apparatus of any one of claims 6 to 26 and/or the running state of each tire.

According to a twenty-eighth aspect of the present invention, there is provided a vehicle control apparatus which comprises vehicle speed detection means to control the running state of a vehicle based on vehicle speed.

According to a twenty-ninth aspect of the present invention, there is provided a vehicle control apparatus for comprising means for controlling the locked state of each wheel such as ABS to control the running state of a vehicle.

According to a thirtieth aspect of the present invention, there is provided a vehicle control apparatus comprising means for controlling the attitude of a vehicle to control the brake unit of each wheel independently so as to control the running state of a vehicle.

According to a thirty-first aspect of the present invention, there is provided a vehicle control apparatus comprising means for controlling the air pressure of each tire to control the running state of a vehicle.

According to a thirty-second aspect of the present invention, there is provided a vehicle control apparatus comprising means for controlling the idling state of each wheel by controlling a brake unit or engine speed.

According to a thirty-third aspect of the present invention, there is provided a vehicle control apparatus comprising means for changing the inter-vehicle distance set value of an automatic driving system based on the above estimated condition of a road surface so as to set an appropriate inter-vehicle distance.

According to a thirty-fourth aspect of the present invention, there is provided a tire wheel comprising the vehicle running state estimation apparatus as set forth in any one of claims 6 to 26 and a electric power generating unit for generating power by the rolling of each tire and supplying power to the above vehicle running state estimation apparatus. Therefore, as the running state of the vehicle can be estimated for a long time without changing the structure of the vehicle body, the running state of the vehicle can be controlled stably.

According to a thirty-fifth aspect of the present invention, there is provided a tire wheel, wherein the above vehicle running state estimation apparatus is mounted to the tire wheel.

According to a thirty-sixth aspect of the present invention, there is provided a tire wheel, wherein the power generating unit comprises a rotor magnetized and rotated by the rolling of each tire, a stator made from a high magnetic permeability material and adjacent to the rotor and a power generating coil installed within a magnetic circuit including the rotor and the stator. Therefore, power supply to the above vehicle running state estimation apparatus is made possible semi-permanently and its functions can be retained for a long time.

According to a thirty-seventh aspect of the present invention, there is provided a tire wheel, wherein the power generating unit comprises means of accumulating electromotive force generated in the above power generating coil. Therefore, stable power supply is possible regardless of the running state of the vehicle.

According to a thirty-eighth aspect of the present invention, there is provided a tire wheel, wherein the rotor is turned by rotating an unbalance weight the gravity center of the rotary cone of which is eccentric to a rotary shaft by the rolling of each tire indirectly or through power transmission means.

According to a thirty-ninth aspect of the present invention, there is provided a tire wheel, wherein an air stream generated by the rolling of each tire is introduced into the above power generating unit and the above rotor is turned by the above introduced air stream.

The other objects, features and advantages of the present invention will become apparent from the following description when taken in conjunction with the accompanying drawings.

BRIEF DESCRIPTION OF THE DRAWINGS

FIG. 3 is a diagram showing time changes in the vibration level of each tire according to Embodiment 1 of the present invention;

FIGS. 5(a) and 5(b) are diagrams showing vibration level distributions in the circumferential direction of the tire on an iced road according to Embodiment 1 of the present invention;

DESCRIPTION OF THE PREFERRED EMBODIMENTS

Preferred embodiments of the present invention will be described hereinbelow with the reference to the accompanying drawings.

Embodiment 1

Figure 1:
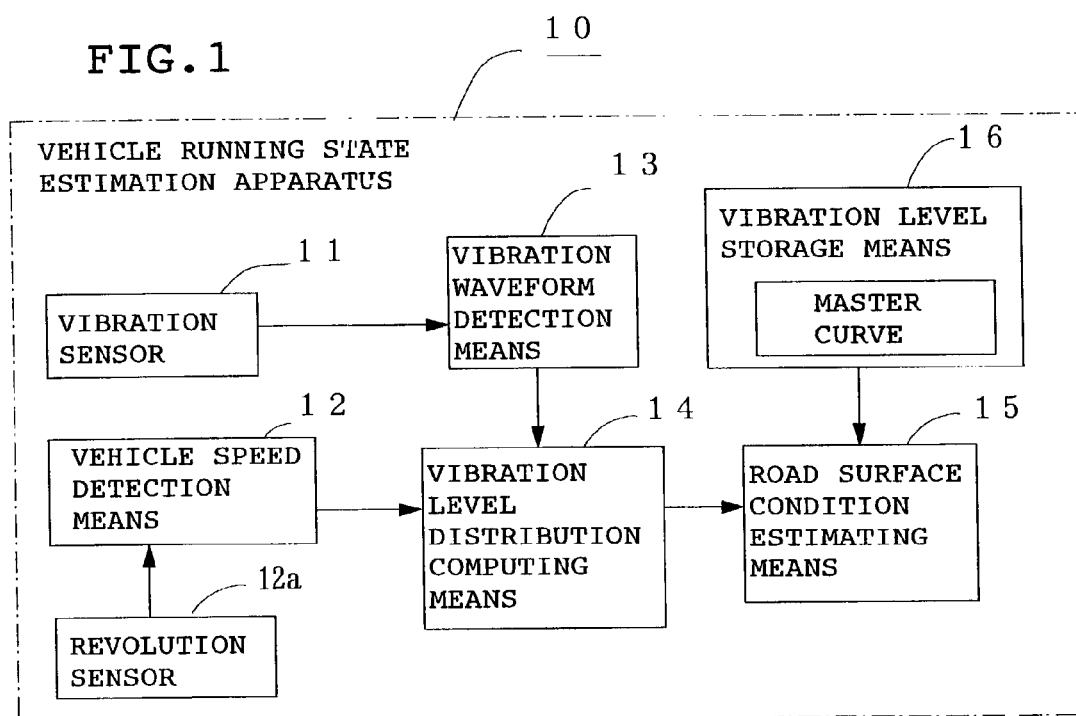
FIG. 1 is a diagram showing the constitution of a vehicle running state estimation apparatus according to Embodiment 1 of the present invention.

FIG. 1 is a block diagram showing the constitution of a vehicle running state estimation apparatus 10 according to Embodiment 1 of the present invention. In the figure, reference numeral 11 denotes a vibration sensor installed on the inner surface of a tire tread, 12 vehicle speed detection means for detecting vehicle speed based on the output pulse of a revolution sensor 12a for detecting the speed of a wheel, 13 vibration waveform detection means for obtaining the waveform of vibration by arranging the output levels (vibration levels) of the above vibration sensor in time sequence, 14 vibration level distribution computing means for obtaining the vibration level distribution of a tire tread by computing the vibration levels in a leading edge portion, a ground contact portion and a trailing edge portion of the tire using the output pulses of the above revolution sensor 12a, and 15 road surface condition estimation means for estimating the condition of a road surface which is one of the running states of a vehicle from the above computed vibration level and the detected vehicle speed using the previously obtained master curve of vibration level depending on vehicle speed stored in vibration level storage means 16.

Figure 2:
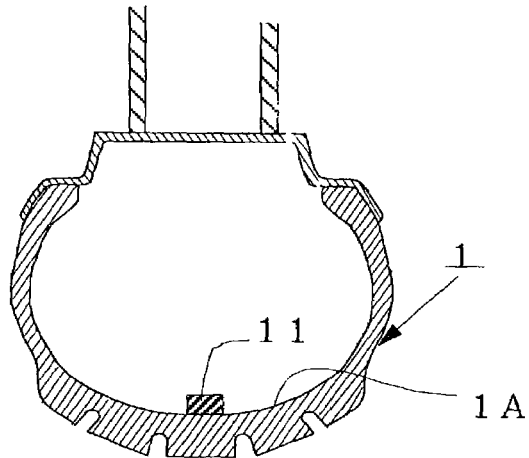
FIGS. 2(a), 2(b) and 2(c) are diagrams showing the installation locations of vibration sensors according to Embodiment 1 of the present invention.
Figure 2:
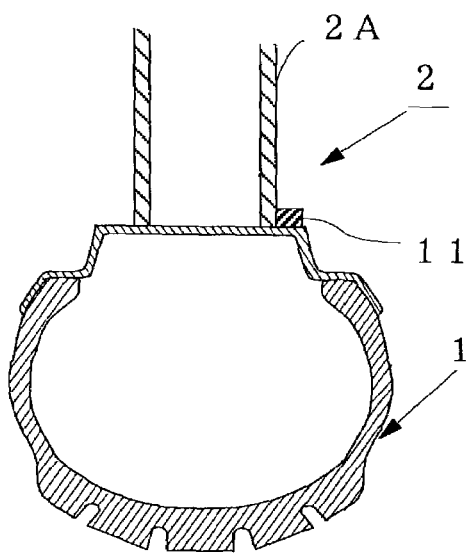
Figure 2:
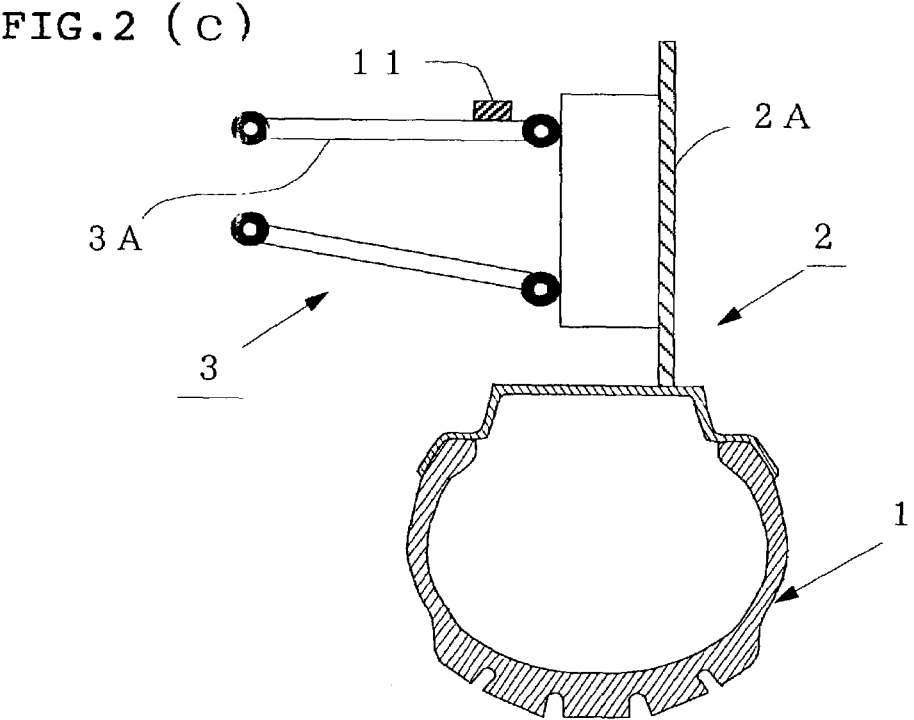

In this Embodiment 1, the vibration sensor 11 for measuring the vibration state of a tire tread is installed on the inner surface 1A of the tire tread (to be simply referred to as "tread" hereinafter) as shown in FIG. 2(a) but the installation location of the vibration sensor 11 is not limited to this. It may be installed on a portion below the spring of a vehicle, for example, the outer side of the rim 2A of a tire wheel portion 2 or the suspension arm 3A of a suspension portion 3 as shown in FIGS. 2(b) and 2(c).

The above master curve of vibration level is drawn by fixing the vibration sensor 11 on the inner surface 1A of the tread 1 of a test vehicle and causing the vehicle to run on road surfaces which differ in road surface friction coefficient μ at a speed V to actually measure the vibration level of the above tread 1.

A description is subsequently given of the method of estimating the condition of a road surface.

First, the vibration level of the tread 1 while running is detected by the vibration sensor 11 installed on the inner surface 1A of the tread 1, a vibration waveform formed by arranging the detected vibration levels in time sequence is obtained by the vibration waveform detection means 13, and a curve (to be referred to as "vibration level distribution" hereinafter) indicative of a vibration level distribution showing vibration detection positions on the time axis of the above waveform as shown in FIG. 3 is drawn by the vibration distribution computing means 14. A power value of vibration level was used as the size of the above vibration level.

Vibration is generated in the leading edge portion (1) before the tread by an impact when the tread 1 contacts the road surface L. In the tread (ground contact portion) (2) where the tread 1 contacts the road surface L, as the tread 1 is confined to the road surface L, vibration is rarely generated. Thereafter, in the trailing edge portion (3), vibration is generated again by releasing the above confinement as soon as the tread 1 departs from the road surface L.

The positions of the above leading edge portion (1), ground contact portion (2) and trailing edge portion (3) and the vehicle speed V are detected by the vehicle speed detection means 12 based on the output pulse of the revolution sensor 12a mounted to each unshown wheel.

The vibration level of the above tread 1 depends mainly on the condition of a road surface on which the vehicle is running and vehicle speed.

Figure 4A:
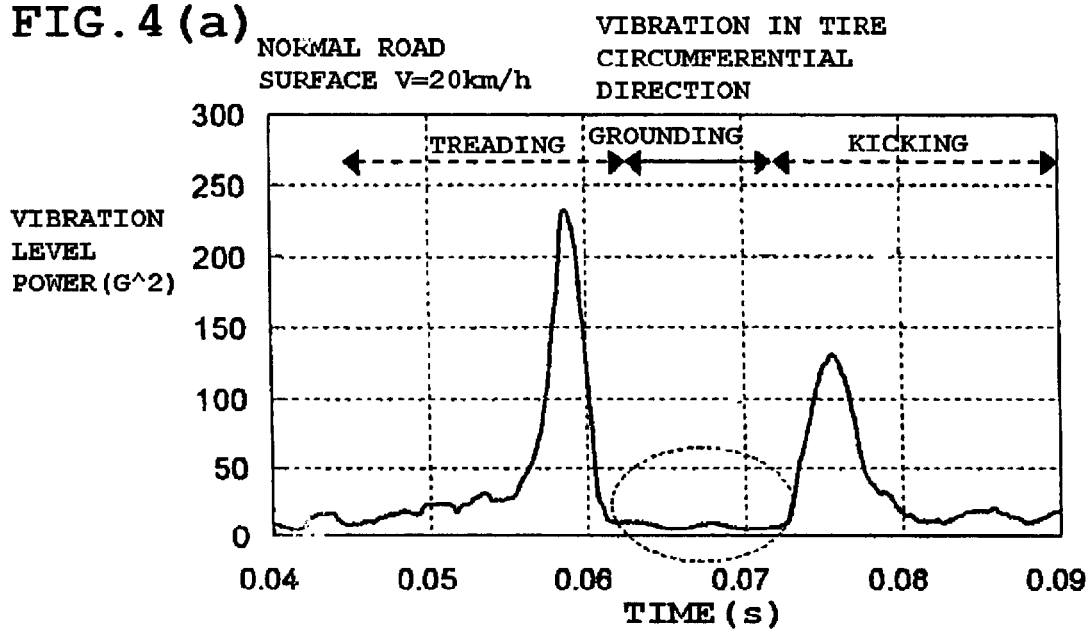
FIGS. 4(a) and 4(b) are diagrams showing vibration level distributions in the circumferential direction of the tire on a regular road surface according to Embodiment 1 of the present invention.
Figure 4B:
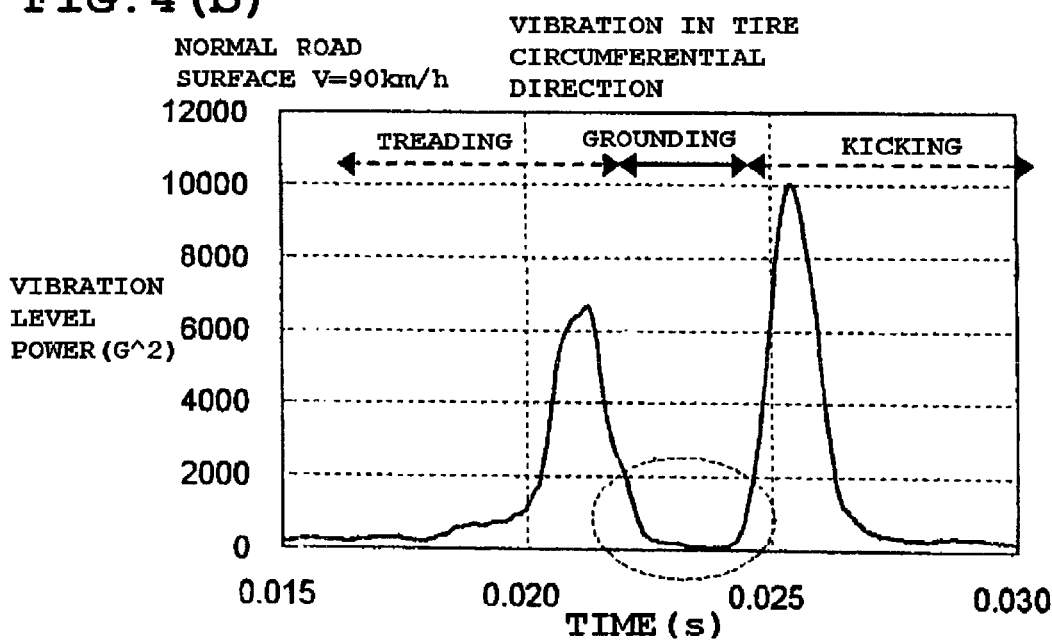

FIG. 4(a) is a diagram showing the vibration level distribution of the tread 1 when a test vehicle runs on a regular dry asphalt road at a low speed (V=20 km/h) and FIG. 4(b) is a diagram showing the vibration level distribution of the tread 1 when the test vehicle runs at a high speed (V=90 km/h).

Meanwhile, when the road surface friction coefficient μ is low, which is generally considered as dangerous, the vibration level distribution of the tread 1 greatly differs from that when the vehicle runs on the above dry asphalt road. For example, even when the vehicle runs on an iced road which is considered to have an extremely low road surface friction coefficient μ at a low speed (V=20 km/h), as constraint from the ground contact surface is small, the tread 1 greatly vibrates in the ground contact portion (2) where vibration is rarely generated as shown in FIG. 5(a). When the vehicle runs on a thick water film at a high speed (V=90 km/h), a hydroplaning phenomenon occurs and the vibration level of the tread 1 further increases in the ground contact portion (2) and the tread 1 greatly vibrates even in the leading edge portion (1) as shown in FIG. 5(b).

This is because the tread 1 greatly vibrates even in the ground contact portion (2) where vibration is rarely generated as constraint from the ground contact surface is small when the road surface friction coefficient μ is low or when the tire is floated by the water film. Particularly when a hydroplaning phenomenon occurs, the vibration of the tread 1 occurs at a position before the essential ground contact surface by a water film or water stream formed in front of the tire.

In this Embodiment 1, the vehicle comprising the vibration sensor 11 mounted on the inner surface 1A of the tread 1 is caused to run on roads which differ in road surface friction coefficient μ at a speed V to obtain the vibration level distribution of the tread 1 from the condition of a road surface and the vehicle speed V as parameters, and this vibration level distribution is stored in the vibration level storage means 16 of the vehicle running state estimation apparatus 10 as a master curve for estimating the condition of a road surface.

Therefore, the vibration level distribution of the tread 1 obtained by the vibration level distribution computing means 14 and the above master curve stored in the above vibration level storage means 16 are compared with each other to estimate the condition of a road surface.

Alternatively, the operation of comparing the measured vibration distribution curve and the master curve is simplified, a threshold value is set for one or a plurality of predetermined vibration levels at detection positions or for a predetermined time range, and the road is estimated as a low-μ road when the above computed vibration level exceeds the above threshold value. For example, the vibration level of the tread 1 in the ground contact portion (2) which satisfies requirements for road surface friction coefficient μ and vehicle speed which are considered as safe is stored in the vibration level storage means 16 as the above threshold value and the computed vibration level of the tread 1 in the ground contact portion (2) while running is compared with the above threshold value to estimate whether the road on which the vehicle is running is a safe high-μ road or slippery low-μ road. It may estimated whether the road is a high-μ road or low-μ road from the two vibration levels of the leading edge portion (1) and the ground contact portion (2).

Alternatively, the ratio (P1:P2:P3) of the power values of vibration level at the positions (1), (2) and (3) under various conditions of a road surface such as a regular dry road and an iced road is stored for each speed and compared with the ratio of the power values of vibration level at the positions (1), (2) and (3) in the computed vibration level distribution to estimate the condition of a road surface.

Embodiment 2

Figure 6:
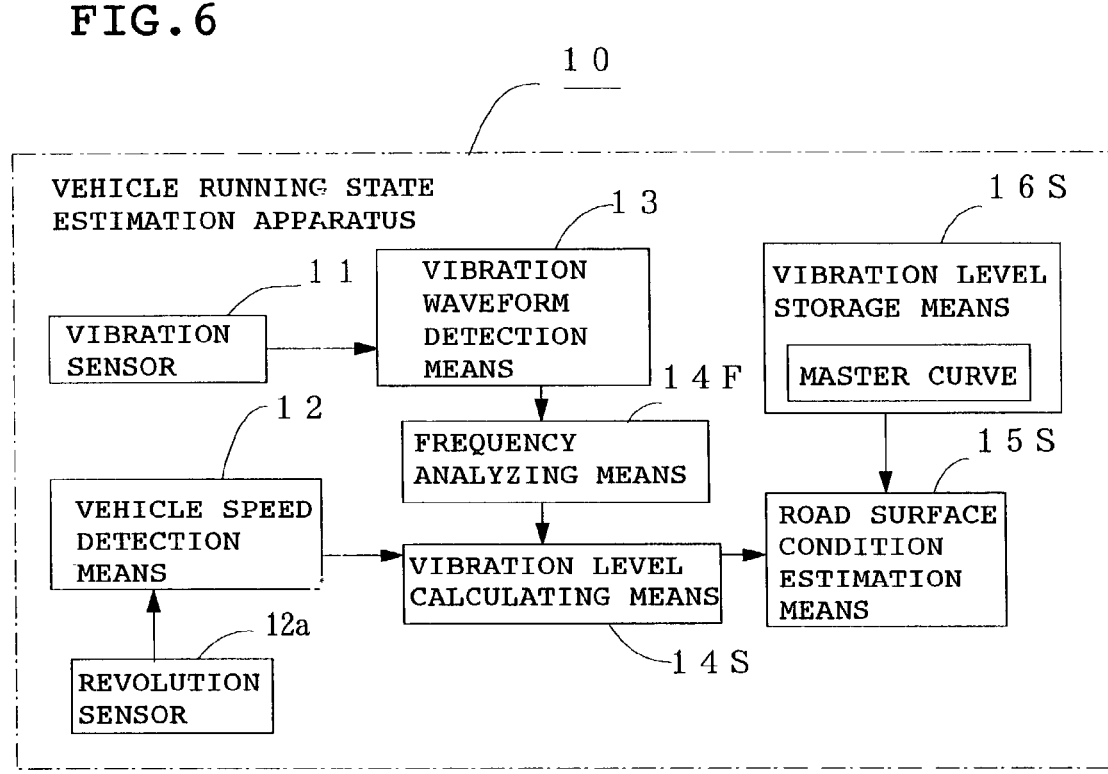
FIG. 6 is a diagram showing the constitution of a vehicle running state estimation apparatus according to Embodiment 2 of the present invention.

In the above Embodiment 1, the vibration levels of a portion below the spring of the vehicle measured by the vibration sensor 11 are arranged in time sequence by the vibration waveform detection means 13 and the vibration level distribution of the tread 1 is obtained by the vibration level distribution computing means 14 to estimate the condition of a road surface. As shown in FIG. 6, frequency analyzing means 14F for obtaining the frequency spectrum of vibration level obtained by converting the frequency of the above vibration level and vibration level calculating means 14S for calculating a vibration level at a predetermined frequency band of the obtained frequency spectrum are provided in place of the above vibration level distribution computing means 14, and further road surface condition estimation means 15S for estimating the condition of a road surface by comparing the vibration level calculated by the above vibration level calculating means 14S with a master curve for estimating the condition of a road surface from the frequency spectrum of vibration level stored in the vibration level storage means 16S is provided to estimate the condition of a road surface from the vibration level at a predetermined frequency band of vibration of a portion below the spring of the vehicle.

Figure 7A:
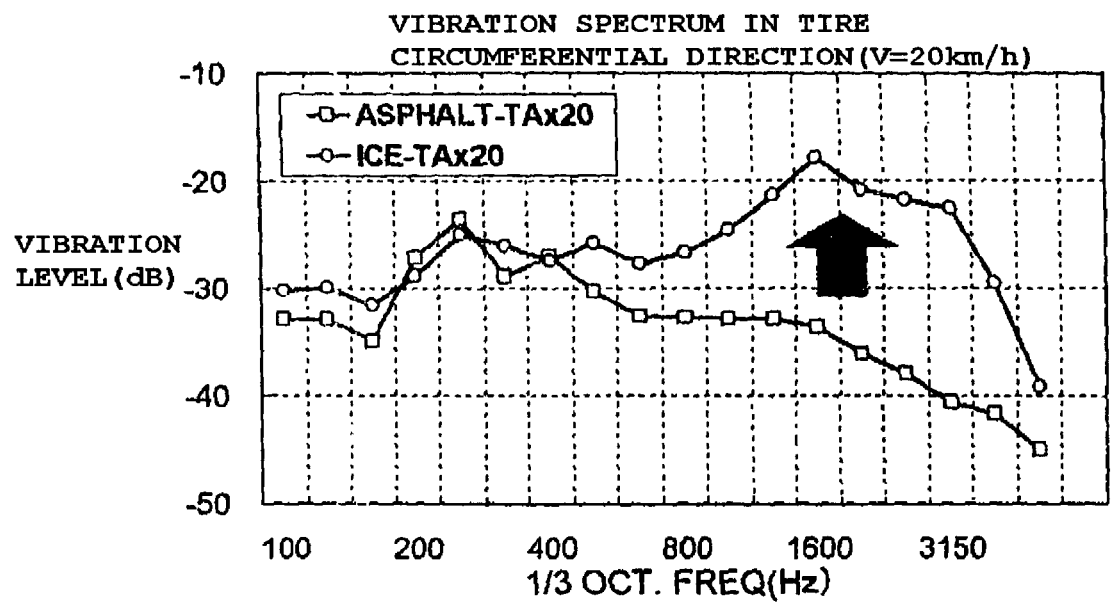
FIGS. 7(a) and 7(b) are diagrams showing the spectra of vibration in the circumferential direction of the tire according to Embodiment 2 of the present invention.
Figure 7B:
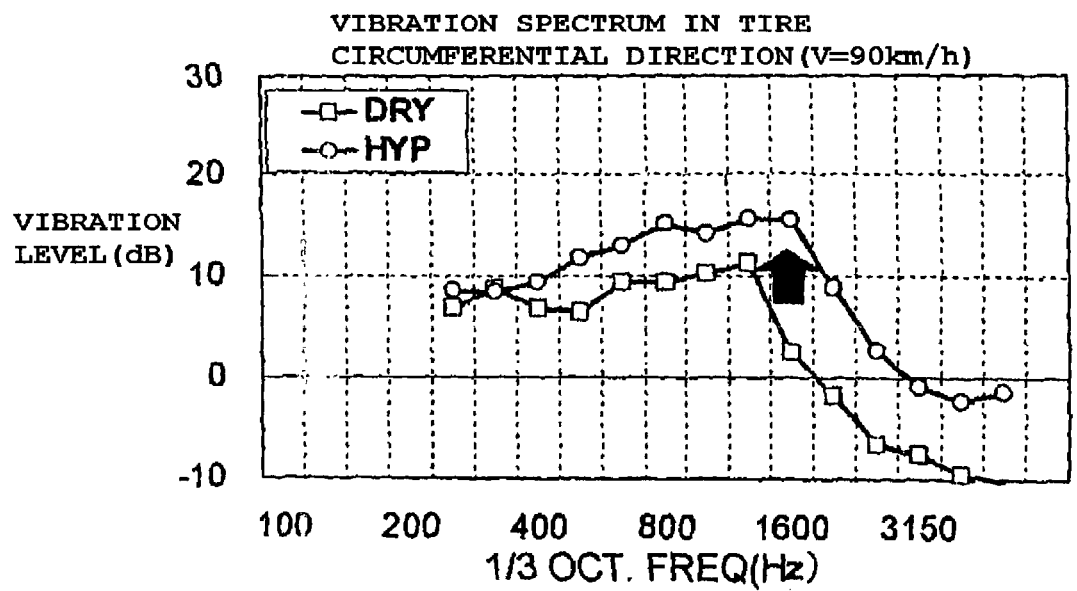

FIGS. 7(a) and 7(b) show the vibration spectra of the tread 1 when the vehicle ran on a regular dry asphalt road and the road surface friction coefficient μ was considered to be extremely low. FIG. 7(a) shows the spectrum of vibration when the vehicle ran on an iced road at a low speed (V=20 km/h) and FIG. 7(b) shows the spectrum of vibration when the vehicle ran on a water film at a high speed (V=90 km/h).

When the frequency components of the above vibration spectra were analyzed, it was found that the vibration level at a frequency of 500 Hz to 2 kHz greatly changes according to the condition of a road surface. This frequency component is identical to the frequency component of vibration right after the tread 1 departs from the tread on a regular road surface and estimated to be caused by the shear or the natural frequency of distortion of a tread block. Then, it is possible to estimate the condition of a road surface by comparing the vibration level at a frequency of about 1.4 kHz which is the natural frequency of the tread block in the above frequency spectrum.

Therefore, the condition of a road surface can be estimated by obtaining the frequency spectrum of vibration level obtained in the same actual vehicle test as in the above Embodiment 1, storing this vibration spectrum as a master curve for estimating the condition of a road surface, frequency converting the vibration waveform of the tread 1 obtained by the vibration waveform detection means 13 by means of the frequency analyzing means 14F, and comparing the vibration level at a predetermined frequency range obtained by the vibration level calculating means 14S with the above master curve stored in the vibration level storage means 16S.

Further, the operation of comparing the measured frequency spectrum with the master curve of the above frequency spectrum is simplified, a vibration level at one or more frequencies close to the frequency of natural vibration of the above tread land portion (block) or a predetermined frequency band is calculated, a threshold value is set for the above vibration level, and it is estimated that the road is a low-μ road when the above vibration level exceeds the above threshold value.

Embodiment 3

Figure 8:
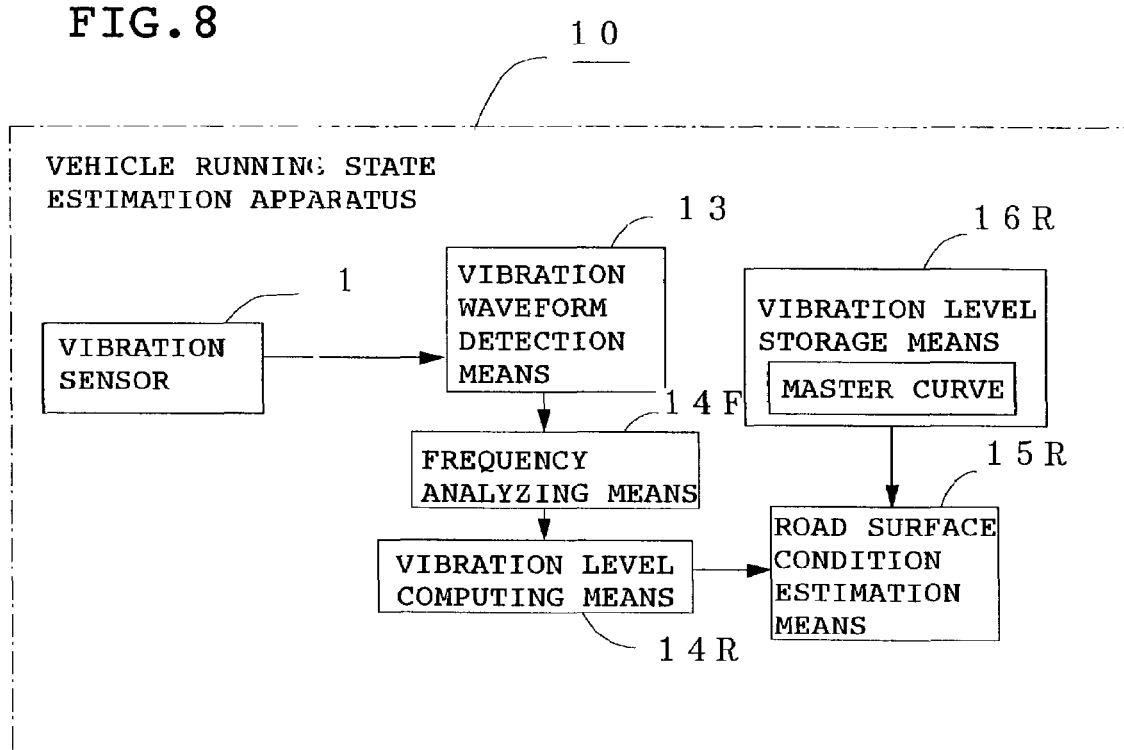
FIG. 8 is a diagram showing the constitution of a vehicle running state estimation apparatus according to Embodiment 3 of the present invention.

In the above Embodiment 2, the condition of a road surface is estimated from the vibration level at a predetermined frequency band calculated by the vibration level calculating means 14S. As shown in FIG. 8, vibration level computing means 14 for computing at least two vibration levels at different frequency bands of the obtained frequency spectrum is provided in place of the above vibration level calculating means 14s, and road surface condition estimation means 15S for estimating the condition of a road surface by comparing the computed value of vibration level computed by the above vibration level computing means 14R with a master curve for estimating the condition of a road surface from the frequency spectrum of vibration level stored in the vibration level storage means 16R is provided to estimate the condition of a road surface.

The above two frequency bands are preferably 300 to 1,000 Hz which is hardly affected by the condition of a road surface and 800 to 5,000 Hz which reflects the slipperiness of a road surface in the spectrum of vibration of a portion below the spring of the vehicle shown in FIGS. 7(a) and 7(b).

The computed value of vibration level is not limited to a value at the above two frequency bands and a computed value of vibration level at three or more frequency bands may be computed to estimate the condition of a road surface.

Figure 9:
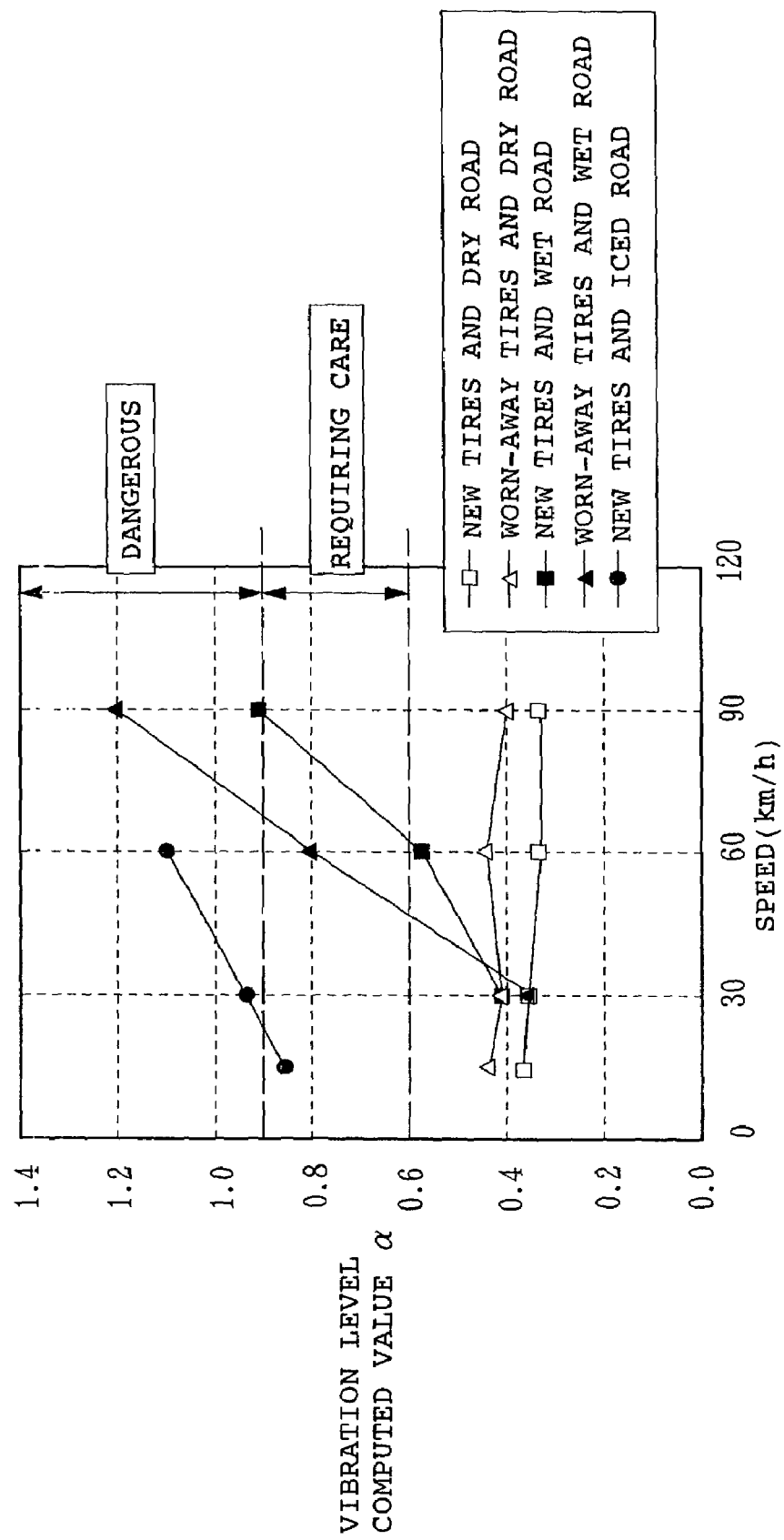
FIG. 9 is a diagram showing the relationship between the computed value of vibration level and vehicle speed under various road surface conditions according to Embodiment 3 of the present invention.

FIG. 9 shows the results of computing the ratio α of the average value of vibration level at a frequency band of 300 to 1,000 Hz to the average value of vibration level at a frequency band of 1,000 to 2,000 Hz when the vehicle runs on a dry road, wet road and iced road at a vehicle speed of 15 to 90 km/h.

On the dry road, the above computed value α is about 0.4 with new tires and worn-away tires regardless of the speed whereas on the wet road, the above computed value α becomes larger as the vehicle speed increases and worn-away tires than new tires. This is because a hydroplaning phenomenon occurs that the vehicle is in a slippery dangerous state when the vehicle runs on the wet road at a high speed with worn-away tires. Meanwhile, on the iced road, the above computed value α is large at 0.8 to 1.1 regardless of the vehicle speed.

Thus, by using a computed value from a vibration level at a plurality of frequency bands, the risk of the condition of a road surface can be judged accurately on a real-time basis regardless of the speed and the abrasion of the tire.

At this point, the reference value which is a threshold value is set using the relationship between the road surface friction coefficient μ and the above computed value α to judge the condition of a road surface (1) as normal when α is equal to or smaller than 0.6, (2) as requiring care when α is larger than 0.6 and equal to or smaller than 0.9 and (3) as dangerous when α is larger than 0.9 (hydroplaning, snow road or iced road). Thus, the slipperiness=risk of the road surface on which the can is running can be judged.

EXAMPLE

The following test was conducted using a vehicle with the vehicle running state estimation apparatus 10 of the present invention and an alarm device which gives an alarm that care must be taken to the driver when the above computed value α obtained by the vibration level computing means 14R exceeds 0.6 and an alarm for a danger when the value a exceeds 0.9.

On a dry road and a wet road having a water depth of 10 mm, the vehicle ran with new tires and worn-away tires at a speed of 30 to 90 km/h and on an iced road, the vehicle ran with new tires at a speed of 15 to 60 km/h.

As a result, on the wet road, an alarm that care must be taken was given when the vehicle ran at a speed of 60 km/h or more with new tires and at a speed of 45km/h or more with worn-away tires and an alarm for a danger was given when the vehicle ran at a speed of 90 km/h or more with new tires and at a speed of 70 km/h or more with worn-away tires. When the vehicle ran with new tires on the iced road, an alarm that care must be taken was given at a speed of 15 km/h or more and an alarm for a danger was given at a speed of 30 km/h or more.

Embodiment 4

In the above Embodiments 1 to 3, the method of estimating the condition of a road surface by detecting the vibration level of a portion below the spring of a vehicle while running has been described. It is also possible to estimate the condition of a road surface from vibration transmission characteristics between two pints of a portion below the spring of the vehicle by detecting the vibration states of the two points.

Figure 10:
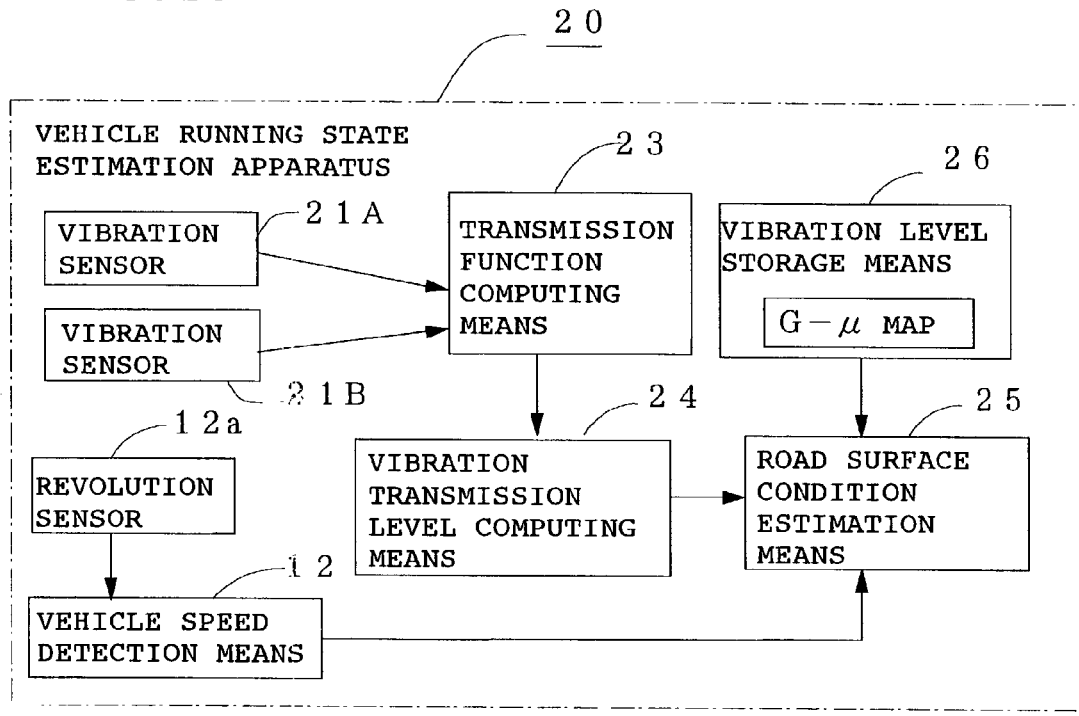
FIG. 10 is a diagram showing the constitution of a vehicle running state estimation apparatus according to Embodiment 4 of the present invention.

FIG. 10 is a block diagram showing the constitution of a vehicle running state estimation apparatus 20 according to Embodiment 4. In the figure, reference symbols 21A and 21B denote first and second vibration sensors mounted at two different points of a portion below the spring of the vehicle, 12 vehicle speed detecting means comprising a revolution sensor 12a, 23 transmission function computing means for computing a vibration transmission function between the above two points from the output levels (vibration levels) of the above first and second vibration sensors 21A and 21B, 24 vibration transmission level computing means for computing a vibration level at a predetermined frequency band from the frequency characteristics of the above transmission function, and 25 road surface condition estimating means for receiving the above computed vibration transmission level and a vehicle speed from the above vehicle speed detecting means 12 and estimating the running state of the vehicle by estimating the condition of a road surface from the above computed vibration transmission level using the previously obtained G-μ map showing the relationship between the vibration transmission level for each vehicle speed and the condition of a road surface, stored in the vibration level storage means 26.

Figure 11:
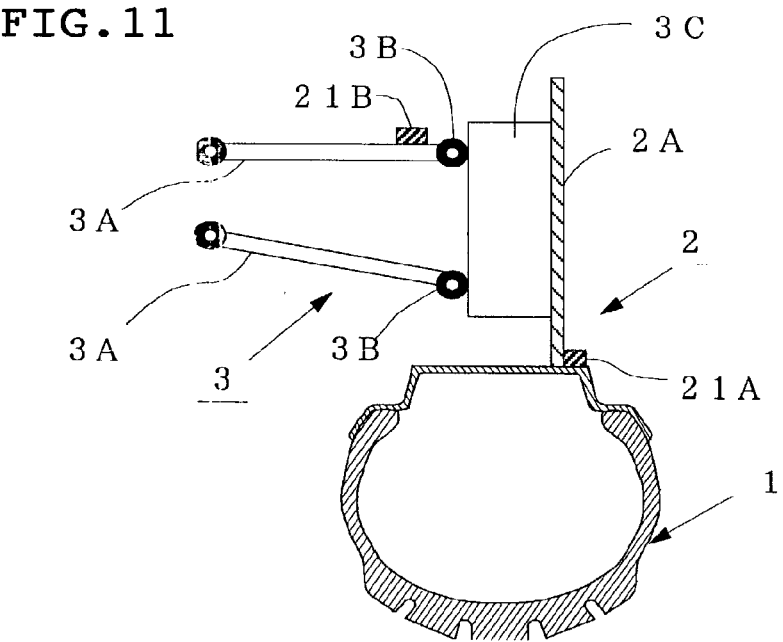
FIG. 11 is a diagram showing the installation locations of vibration sensors according to Embodiment 4 of the present invention.

The two points which differ from each other in relative vibration characteristics and are required for obtaining vibration transmission characteristics are preferably two points sandwiching a buffer member. Therefore, in this Embodiment 4, as shown in FIG. 11, the above vibration sensors 21A and 21b are mounted on the outer side of the rim 2A of a tire wheel portion 2 and on the suspension arm 3A of a suspension 3. The suspension arm 3A on which the above vibration sensor 21B is mounted is connected to a hub portion 3C through a proximal rubber bush 3B, whereby the two vibration sensors 21A and 21B are arranged with the buffer member therebetween.

Figure 12A:
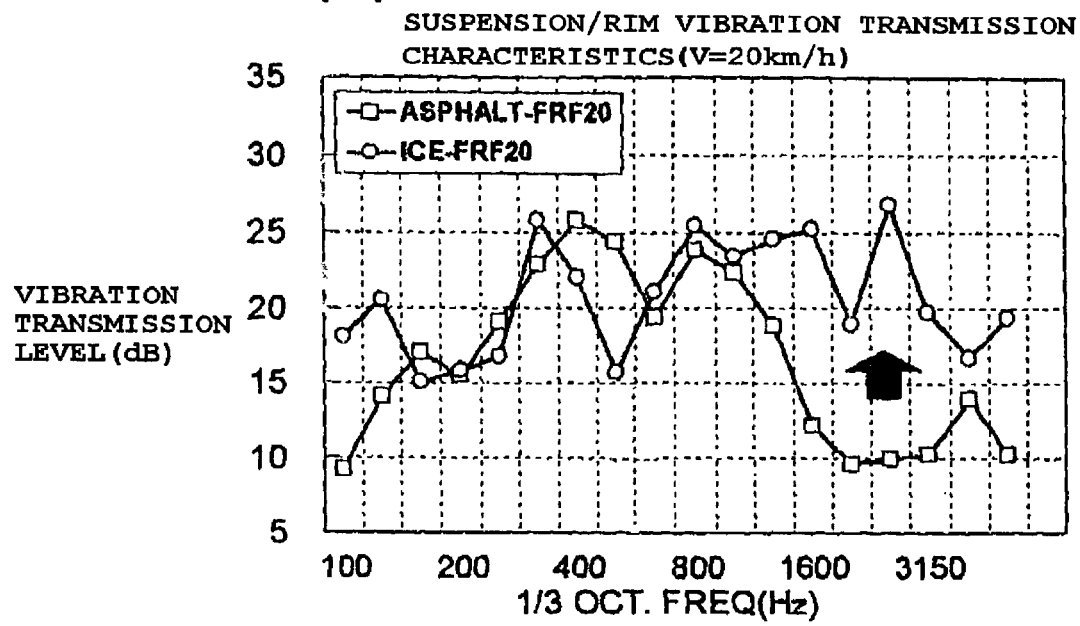
FIGS. 12(a) and 12(b) are diagrams showing the vibration spectra of vibration transmission level according to Embodiment 4 of the present invention.
Figure 12B:
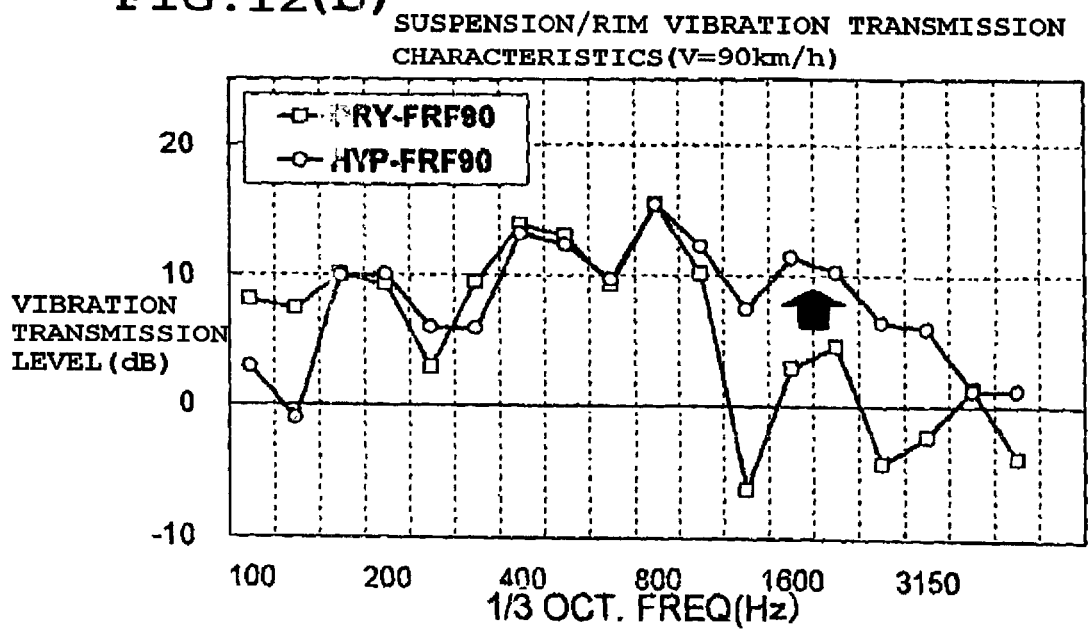

FIGS. 12(a) and 12(b) show the measurement results of vibration transmission levels measured by the first and second vibration sensors 21A and 21B mounted on the tire wheel portion 2 and the suspension portion 3 which are portions below the spring of the vehicle, respectively. FIG. 12(a) shows the vibration transmission levels at a low speed (V=20 km/h) and FIG. 12(b) shows the vibration transmission levels at a high speed (V=90 km/h).

As obvious from the figures, the vibration transmission levels on an iced road and a water film are extremely higher at a frequency band of 500 Hz to 2 kHz than the vibration transmission levels on a regular dry asphalt road. This is because the wheel including the tire is excited by the vibration within the tread of the tread 1, and vibration between the tire and the wheel and between the suspension and the wheel is easily transmitted as constraint from the road surface of the tread 1 is small due to a low-μ road, resulting in an increase in vibration transmission level at the above frequency band.

Therefore, by monitoring the vibration transmission level at the above band, the condition of a road surface can be estimated. Stated more specifically, the frequency spectra of vibration transmission levels on various road surface conditions are previously obtained and stored as a master curve for estimating the condition of a road surface, a vibration transmission function obtained by the transmission function computing means 23 is frequency converted, and the obtained frequency spectrum is compared with the above master curve of the frequency spectra to estimate the condition of a road surface. Alternatively, the vibration transmission level at a frequency band of 500 Hz to 2 kHz is calculated, a threshold value is set for the above vibration transmission level and it is estimated that the road is a low-μ road when the above vibration transmission level exceeds the above threshold value.

In this Embodiment 4, unlike the prior art described in the above Japanese Laid-open Patent Application No. 11-94661, the vibration transmission level between two points of the portion below the spring of the vehicle is monitored, thereby making it possible to estimate the condition of a road surface with high accuracy without being influenced by disturbance such as the roughness of the road surface.

Figure 13:
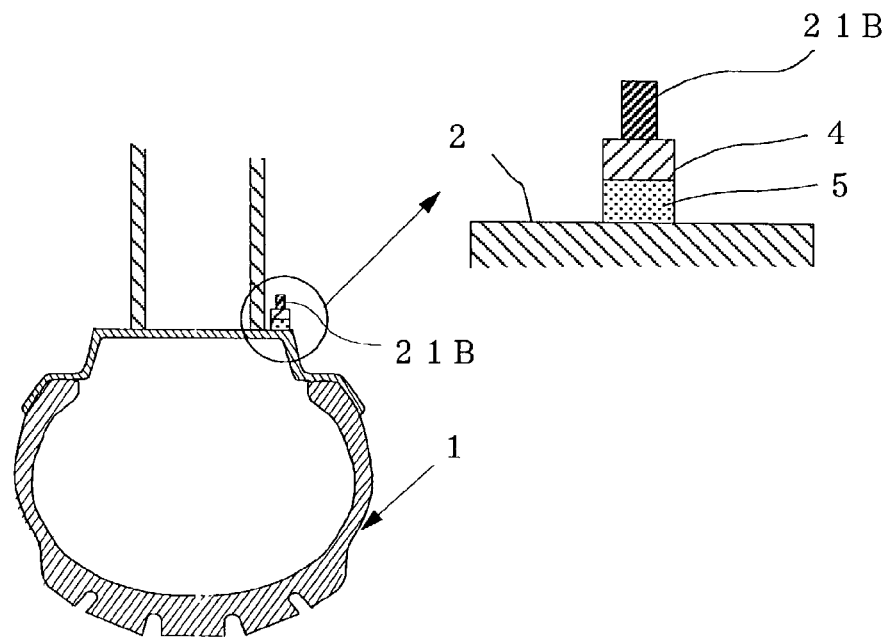
FIG. 13 is a diagram showing another installation location of a vibration sensor according to Embodiment 4 of the present invention.

As shown in FIG. 13, a metal "float" 4 may be mounted to the tire wheel portion 3 through a buffer member 5 made from an elastic material and the second vibration sensor 21B may be mounted on this "float" 4 to measure vibration transmission characteristics between the above tire wheel portion 3 and the above "float" 4 with the first vibration sensor 21A and the above second vibration sensor 21B mounted on the above tire wheel portion 3, respectively.

The buffer member 5 may be a stabilizer or a link bush or may be bonded to a portion below the existing spring. The buffer member is made from rubber having elastic characteristics (silicon-, olefin- or phenylene-based) or resin (urethane- or Teflon-based).

In the above Embodiments 1 to 4, the regular dry asphalt road and the road having a low road surface friction coefficient μ have been taken as examples of the road. The type of the road is not limited to these and a road is suitably set according to the district and environment where the vehicle is used and the conditions of the road surface may be classified into three or more estimated conditions of the road surface, for example, (1) high-μ road ($\mu \geq 0.6$), (2) intermediate-μ road ($0.3 \leq \mu < 0.6$), and (3) low-μ road ($\mu < 0.3$).

Since the vibration level of the above Embodiments 1 to 3 and the vibration transmission level of the above Embodiment 4 are changed by times variations in the air pressure and temperature of each tire, rubber hardness or the abrasion amount of the tread. If the above master curve or the threshold value might be changeable by the above data values, the estimation accuracy of the condition of a road surface could be further improved.

In the above Embodiments 1 to 4, the condition of a road surface is estimated from the vibration level or vibration transmission level using the master curve of vibration waveforms or frequency spectra of various road surface conditions. A running test and a braking test are conducted on various road surface conditions, vibration levels or vibration transmission levels at those times are measured, and the road surface friction coefficient μ between the tire and the test road surface is calculated from a braking distance on the road surface to draw a master curve of vibration waveforms or frequency spectra at each road surface friction coefficient μ, thereby making it possible to construct a road surface condition estimation apparatus capable of estimating the road surface friction coefficient μ using the above master curve from the vibration level or vibration transmission level measured while running.

Figure 14:
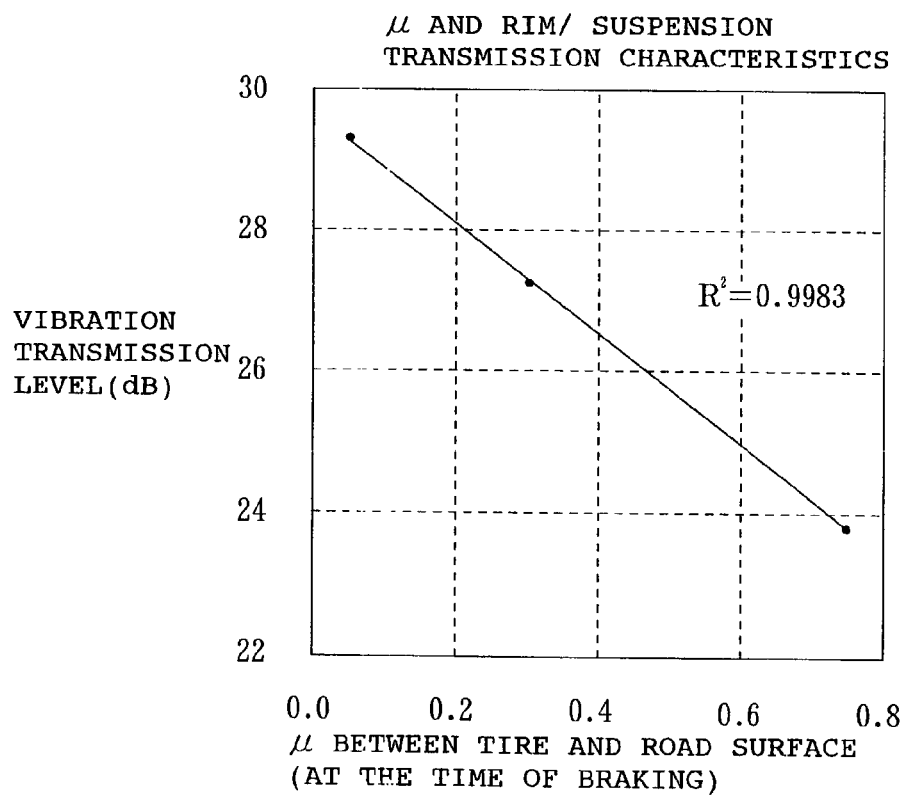
FIG. 14 is a diagram showing the relationship between road surface friction coefficient μ and vibration transmission level according of Embodiment 4 of the present invention.

For example, FIG. 14 plots the road surface friction coefficient μ obtained from the braking distance on an iced road, snow road and dry asphalt road on the axis of abscissas and the size of vibration transmission level at 50 Hz to 2 kHz of the vibration transmission function described in the above Embodiment 4 (at the time of running at a fixed speed of 20 km/h) on the axis of ordinates. Thus, since the above road surface friction coefficient μ and the vibration transmission level are closely correlative to each other ($R^2=0.9983$), the road surface friction coefficient μ can be estimated from the vibration transmission level measured while running with high accuracy.

Embodiment 5

In the above Embodiments 1 to 4, the method of estimating the condition of a road surface from the vibration level or vibration transmission level of a portion below the spring of the vehicle has been described. When it is estimated from the above vibration level or vibration transmission level how slippery the surface of the road is and the condition of the road surface is estimated to be slippery, it is possible to warn the driver or passenger of the risk.

Figure 15:
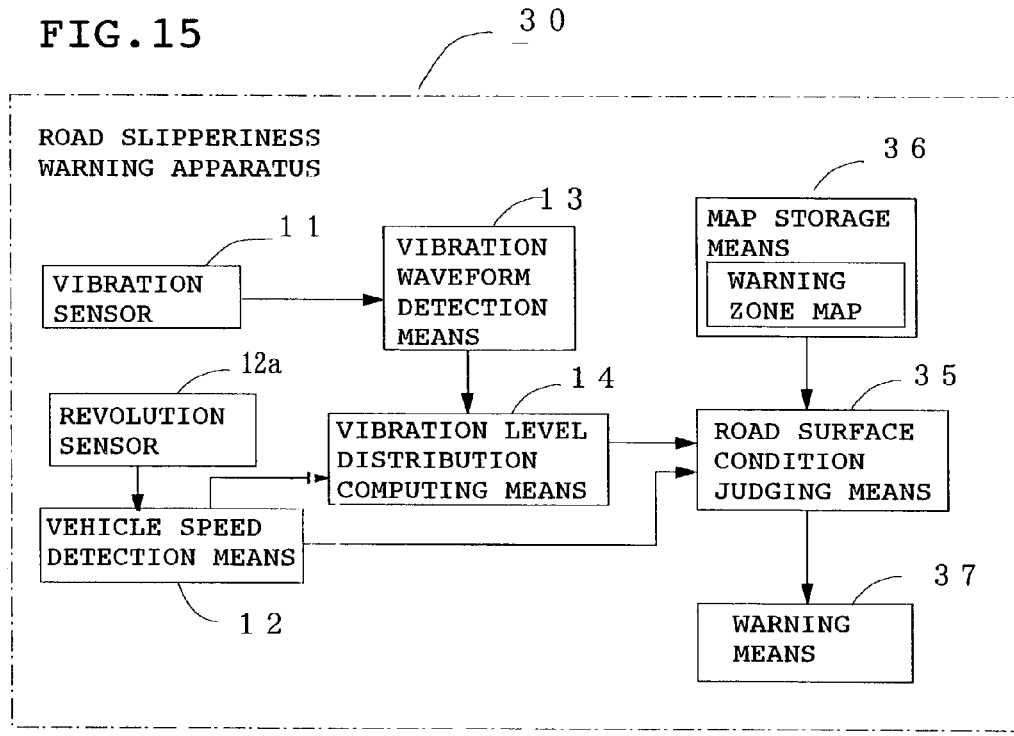
FIG. 15 is a diagram showing the constitution of a road slip alarm according to Embodiment 5 of the present invention.

FIG. 15 is a diagram showing the constitution of a road slipperiness warning apparatus 30 according to Embodiment 5. The road slipperiness warning apparatus 30 comprises map storage means 36 for storing a warning zone map having two warning zones Z1 and Z2 surrounded by vehicle speed V and the size of vibration level shown in FIG. 16 in place of the vibration level storage means 16 of the above Embodiment 1, road condition judging means 35 for judging where the vibration level of the tread 1 obtained by the vibration distribution computing means 14 and vehicle speed are positioned in the above warning zone map in place of the road surface condition estimation means 15 of the above Embodiment 1, and further warning means 37 for warning the driver or passenger of a risk when the measured vibration level and vehicle speed are in the above warning zone Z1 or Z2.

The road slipperiness warning apparatus 30 of Embodiment 5 activates the warning means 37, for example, turns on and off an unshown red lamp when the vibration level corresponding to the vehicle speed of the tread 1 is in the warning zone Z1 of the first stage and sounds an alarm and turns on and off the above red lamp when the above vibration level is in the warning zone Z2 of the second stage. Thus, the road slipperiness warning apparatus 30 warns the driver or passenger of the risk of the road surface. Since the risk of the condition of the road surface can be thereby informed of the driver while running, the driver can take early operation to decelerate and a reduction in the number of accidents can be expected.

EXAMPLE

Figure 16:
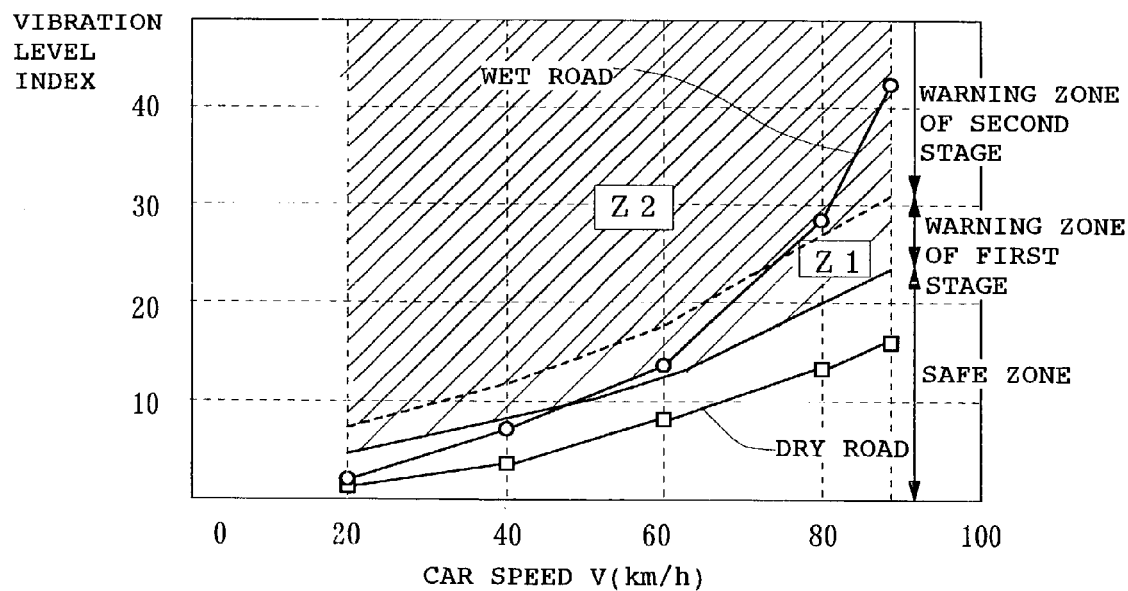
FIG. 16 is a diagram showing a warning zone map according to Embodiment 5 of the present invention.

When a test vehicle with the above road slipperiness warning apparatus 30 was caused to run on a dry asphalt road or wet road (water pool having a depth of 10 mm) by increasing the vehicle speed to 20, 40, 60, 80 and 90 km/h gradually, the vibration level of the tread 1 rose as the vehicle speed increased on the regular dry asphalt road (marked with) and the wet road (marked with O) where hydroplaning easily occurs as shown in FIG. 16. Particularly when the road was wet and the vehicle speed was high, the above vibration level jumped up. On the wet road, the warning of the first stage was given when the vehicle speed became 60 km/h and the warning of the second stage was given when the vehicle speed became 80 km/h or more. Thus, it was confirmed that the object of the present invention could be attained.

In the above Embodiment 5, a warning was given by estimating the slipperiness of the road by obtaining the vibration level distribution of a portion below the spring of the vehicle measured by the vibration sensor like the above Embodiment 1. Like the above Embodiments 2 and 3, the slipperiness of the road may be estimated from the vibration level at a predetermined frequency band or the value obtained by carrying out an operation on at least two vibration levels at different frequency bands of the frequency spectrum of vibration level obtained by frequency converting the above vibration level.

Embodiment 6

In the above Embodiment 5, the risk of the road condition is directly judged from the measured vibration level of the portion below the spring of the vehicle. The vibration states of two points of the portion below the spring of the vehicle are detected and the slipperiness of the road surface is estimated from the vibration transmission level between the above two points to give a warning.

Figure 17:
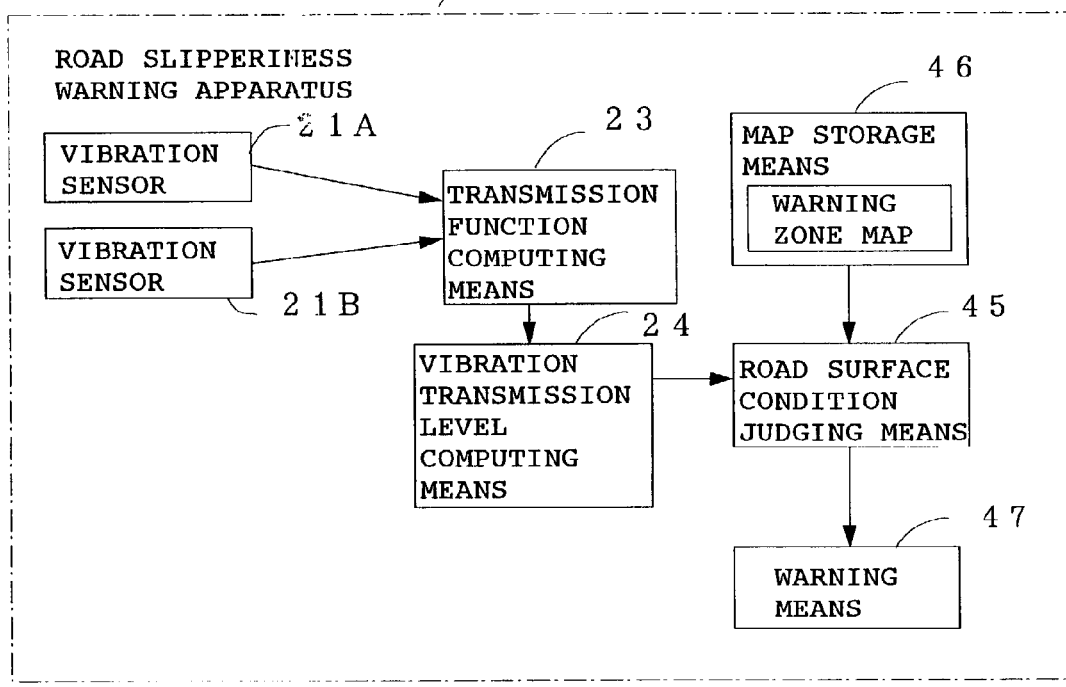
FIG. 17 is a diagram showing the constitution of a road slipperiness warning apparatus according to Embodiment 6 of the present invention.
Figure 18:
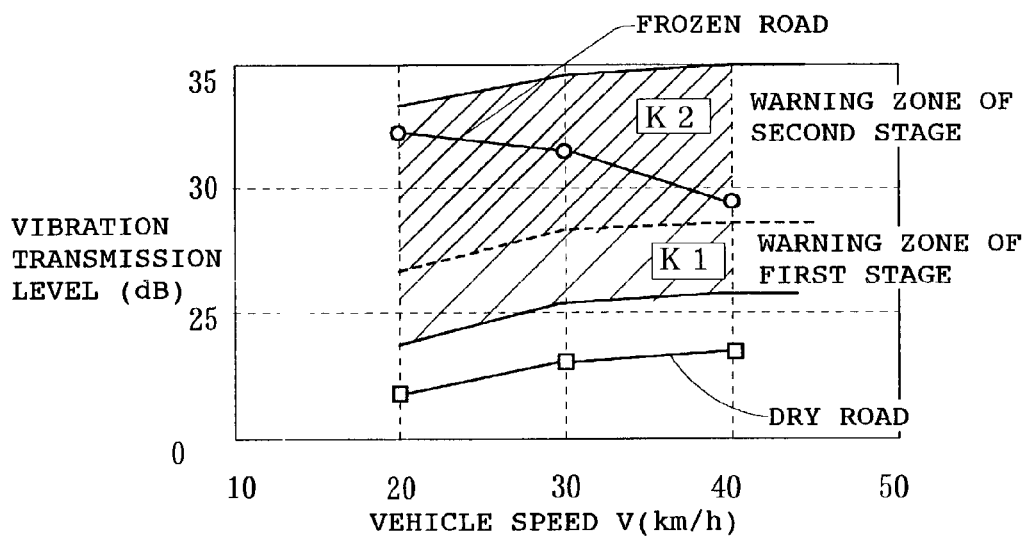
FIG. 18 is a diagram showing a warning zone map according to Embodiment 6 of the present invention.

FIG. 17 is a diagram showing the constitution of a road slipperiness warning apparatus 40 according to Embodiment 6 of the present invention. The road slipperiness warning apparatus 40 comprises map storage means 46 for storing a warning zone map having two warning zones K1 and K2 surrounded by the vehicle speed V and the vibration transmission level G shown in FIG. 18 in place of the vibration level storage means 26 of the above Embodiment 4, road surface condition judging means 45 for judging where the vibration transmission level obtained by the vibration transmission level computing means 24 and vehicle speed are located in the above warning zone map in place of the road surface condition estimation means 25, and further warning means 47 for warning the driver or passenger of a risk when the above measured vibration transmission level and vehicle speed are in the above warning zone K1 or K2. When the vibration level of the tread and the vehicle speed are in the warning zone K1 of the first stage or the warning zone K2 of the second stage, the warning means 47 is activated to warn the driver or passenger of the risk of the road surface.

EXAMPLE

When a test vehicle with the above road slipperiness warning apparatus 40 was caused to run on a dry asphalt road and a frozen road at a fixed speed of 20, 30 or 40 km/h, a warning of the second stage was given at all the speeds on the frozen road. Thus, it was confirmed that the object of the present invention could be attained.

In the above Embodiments 5 and 6, the risk of the road surface condition is directly judged from the measured vibration transmission level. An estimated road surface condition computing apparatus similar to the vehicle running state estimation apparatuses 10 and 20 of the above Embodiments 1 to 4 may be constructed and a risk may be warned to the driver or passenger according to the condition of a road surface computed by the estimated road surface condition computing apparatus. In this case, it is needless to say that the above road surface conditions and the warning zones must be set to relate the estimated road surface conditions with the set warning zones.

Embodiment 7

Figure 19:
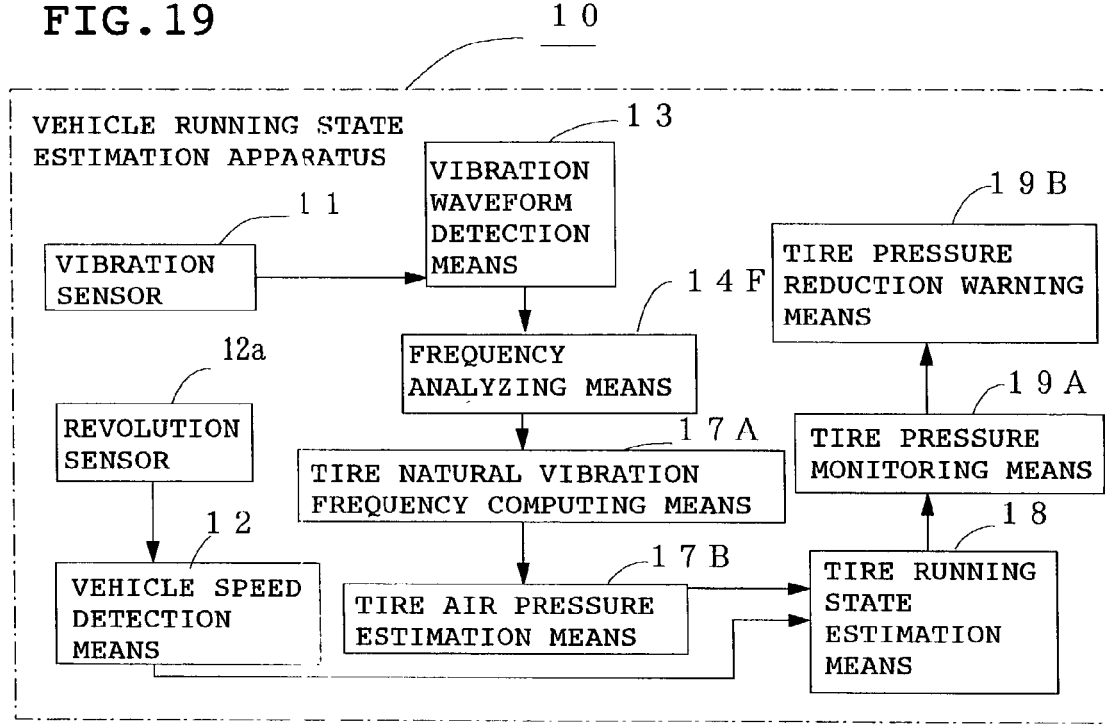
FIG. 19 is a diagram showing the constitution of a vehicle running state estimation apparatus according to Embodiment 7 of the present invention.

In the above Embodiment 2, the method of estimating the condition of a road surface by calculating a vibration level at a predetermined frequency band from the frequency spectrum of the vibration level of a portion below the spring of the vehicle obtained by the frequency analyzing means 14F has been described. As shown in FIG. 19, tire natural vibration calculating means 17A for calculating the frequency of natural vibration of each tire from a vibration level at a frequency band of 200 Hz or less of the detected vibration level, tire air pressure estimation means 17B for estimating the air pressure of each tire from the calculated frequency of natural vibration of the tire and tire running state estimation means 18 for estimating the running state of each tire from the estimated air pressure of the tire are provided to estimate the running state of the tire which is one of the running states of the vehicle.

Figure 20:
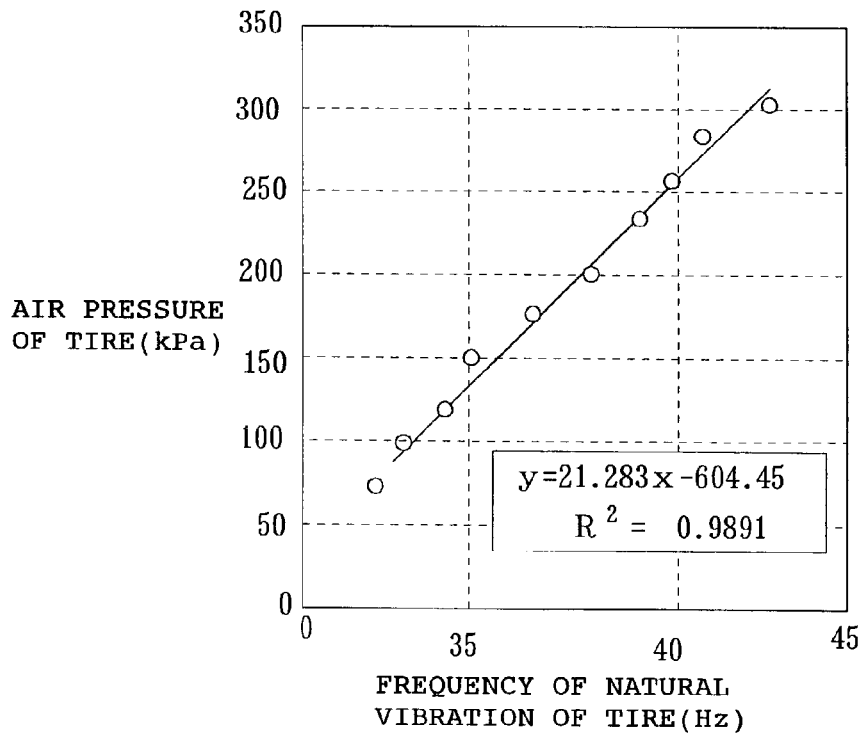
FIG. 20 is a diagram showing the relationship between the frequency of natural vibration and the air pressure of the tire according to Embodiment 7 of the present invention.

FIG. 20 shows the relationship between the frequency of natural vibration of the tire (Hz) and the air pressure (MPa) of the actual tire. Since the above frequency of natural vibration of the tire and the air pressure of the tire are closely correlative to each other ($R^2$=0.9891), the vibration level of a portion below the spring of the vehicle is detected and frequency analyzed so that the air pressure of the tire can be estimated from a vibration level at a frequency band of 200 Hz or less of the detected vibration level with high accuracy.

In this embodiment, tire pressure monitoring means 19A for monitoring the pressure of the tire while running using the above estimated air pressure and tire pressure reduction warning means 19B for warning the passenger of a reduction in the pressure of the tire when the air pressure monitored by the above tire pressure monitoring means 19A falls below a predetermined value are provided to warn the passenger of a reduction in the pressure of the tire. Thereby, the running state of the tire can be estimated and when the pressure of the tire monitored while running falls below a predetermined value, this can be warned to the passenger, thereby making it possible to improve the safety of the vehicle.

Embodiment 8

Figure 21:
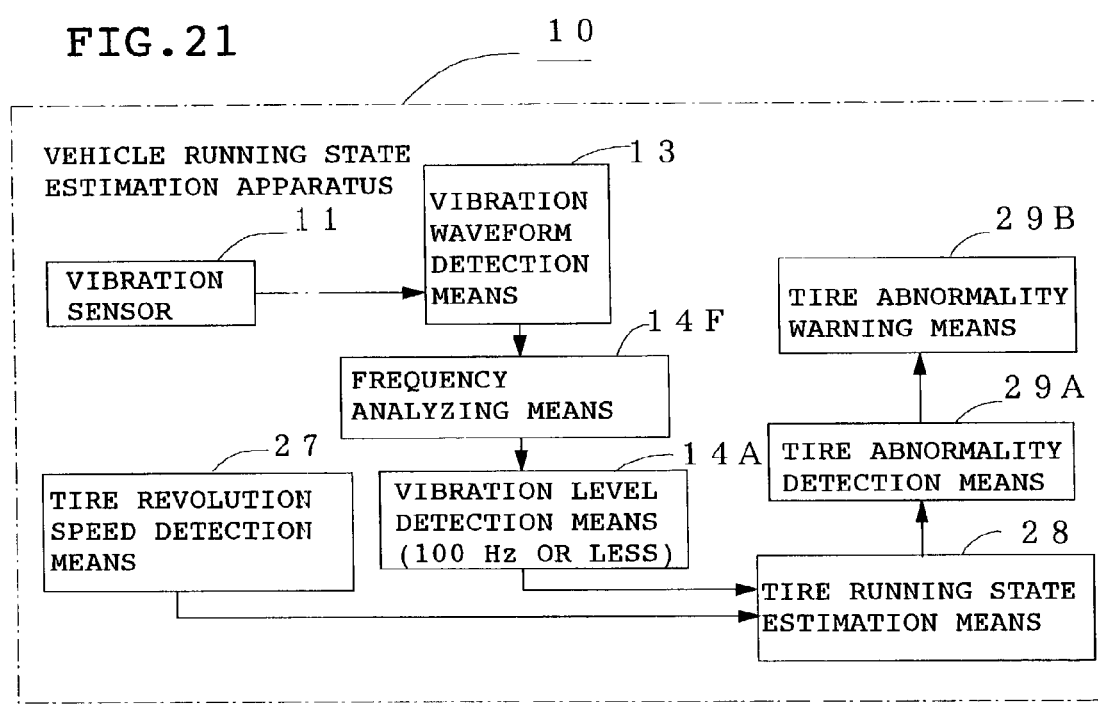
FIG. 21 is a diagram showing the constitution of a vehicle running state estimation apparatus according to Embodiment 8 of the present invention.

In the above Embodiment 7, the air pressure of the tire is estimated by calculating the frequency of natural vibration of the tire from a vibration level at a frequency band of 200 Hz or less of the vibration level of a portion below the spring of the vehicle by means of the tire natural vibration calculating means 17A and the tire air pressure estimation means 17. As shown in FIG. 21, tire revolution speed detection means 27, tire running state estimation means 28 for estimating the state of the tire while running by calculating the average value of vibration level changing by the revolution speed of the tire at a frequency band of 100 Hz or less of the detected vibration level, tire abnormality detection means 29A for judging that the tire is abnormal when the calculated average value of vibration level exceeds the preset reference value and tire abnormality warning means 29B for warning the passenger of the abnormality of the tire based on the detection result of the above tire abnormality detection means 29A are provided to estimate the running state of the tire and to judge the abnormality of the tire, thereby making it possible to warn the passenger of this abnormality.

For example, when part of the tread portion peels off, air in the inside of the tire is excited by the generation of vibration each time the part contacts the surface of a road. As the initial peel-off trouble occurs at one site on the outer surface of the tire, vibration generated thereby is periodical according to the revolution of the tire. The cycle is about 14 Hz (primary), 28 Hz (secondary) and 42 Hz (tertiary) at a speed of 100 km/h in the case of a tire for a general passenger vehicle. The above peak generally appears by the ground contact of the tire even while running but when a peel-off trouble occurs at one site on the outer surface of the tire, the above peak level is extremely high, whereby it is estimated that something abnormal occurs in the tire.

Therefore, a vibration level at a frequency band of 100 Hz or less (for example, 14 Hz, 28 Hz or 42 Hz) of the vibration level of a portion below the spring of the vehicle is calculated by the above tire running state estimation means 28, it is judged that the tire is abnormal condition when the average value of the calculated vibration level exceeds a predetermined reference value, and this information is sent to the tire abnormality detection means 29A to warn the occurrence of abnormality in the tire to the passenger.

Figure 22:
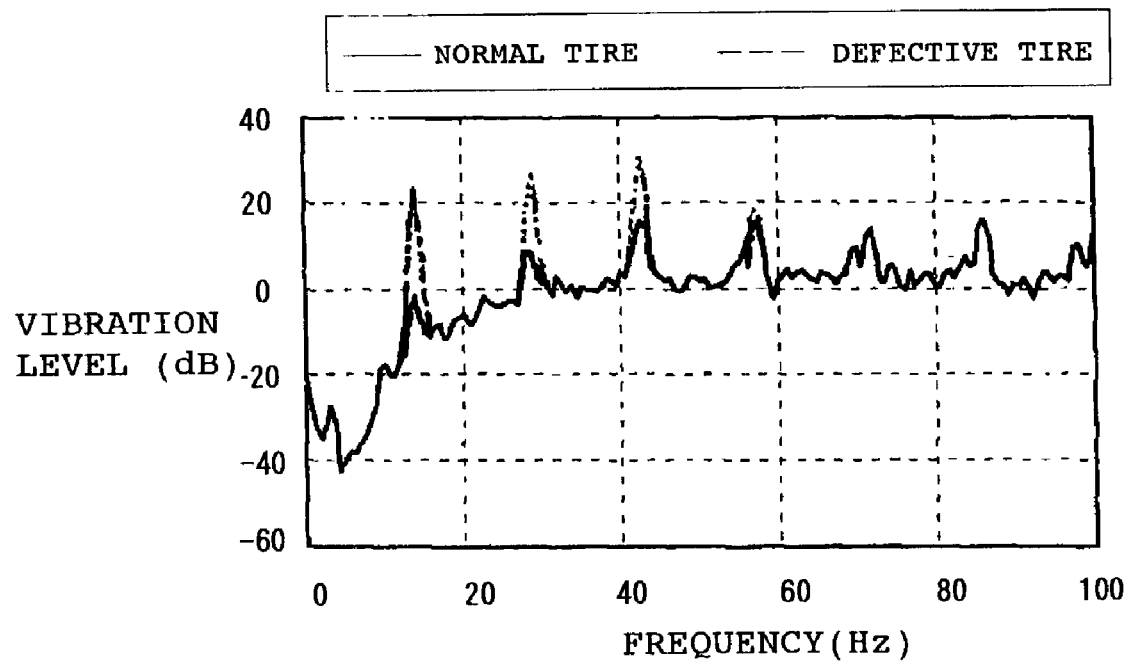
FIG. 22 is a diagram showing a detection example of a tire peel-off trouble according to Embodiment 8 of the present invention.

FIG. 22 is a diagram showing the result of comparison between the vibration level (dB) of a defective tire having a cut at one site on the outer surface between the tire tread and the steel belt and that of a normal tire. Stated more specifically, the above defective tire and the normal tire were caused to run on an indoor drum at a fixed speed of 100 km/h to measure their vibration levels and analyze the frequencies of the vibration levels.

As described above, even in the case of the normal tire, peaks appear at frequencies of about 14 Hz (primary), 28 Hz (secondary), 42 kHz (tertiary), . . . whereas in the case of the defective tire, as shown by a broken line in the figure, the sizes of the peaks are about 20 dB larger than those of the normal tire. The peaks are much higher than the peaks of the normal tire at the above frequencies, which are set as references for detecting a tire trouble and a tire trouble can be detected by detecting the vibration level of the portion below the spring of the vehicle.

The above reference value is set to a range of 1.2 to 5 times the vibration level at a reference decision frequency $Fn=n \times V/(2\pi r)$ when the vehicle runs at a predetermined vehicle speed V while no abnormality occurs in the tire to detect the above abnormality with high accuracy. In the above equation, r is the rolling radius of the tire and n is a natural number.

The above reference value can be changed by time variations in temperature, the abrasion amount of the tire tread or the deterioration of the hardness of rubber.

Embodiment 9

Figure 23:
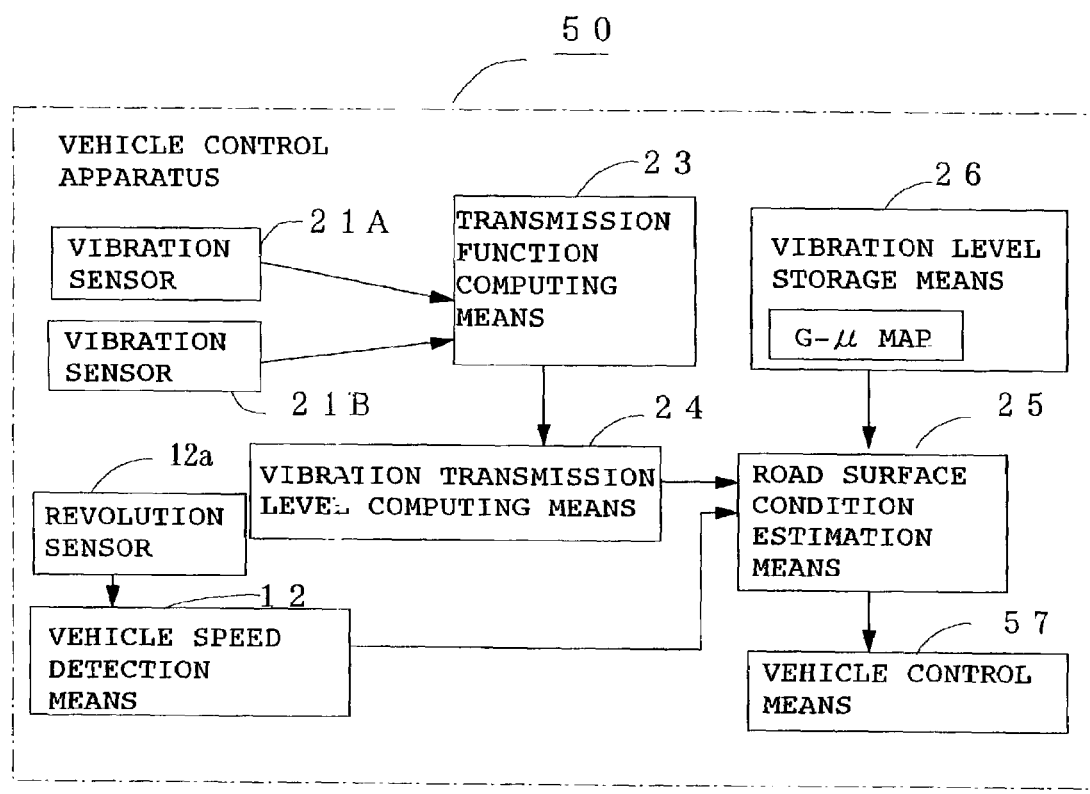
FIG. 23 is a diagram showing the constitution of a vehicle control apparatus according to Embodiment 9 of the present invention.

FIG. 23 is a diagram showing the constitution of a vehicle control apparatus 50 according to Embodiment 9. The vehicle control apparatus 50 comprises vibration sensors 21A and 21B installed at two different points of a portion below the spring of the vehicle, vehicle detection means 12, transmission function computing means 23 for computing a vibration transmission function between the above two points from the output levels (vibration levels) of the above vibration sensors 21A and 21B, vibration transmission level computing means 24 for computing a vibration level at a predetermined frequency band from the frequency characteristics of the above transmission function, road surface condition estimation means 25 for receiving the above computed vibration transmission level and a vehicle speed from the above vehicle speed detection means 12 and estimating the condition of a road surface using the previously obtained G-μ map showing the relationship between vibration transmission level for each vehicle speed and the condition of a road surface stored in the vibration level storage means 26, and vehicle control means 57 for controlling the running state of the vehicle based on the estimated condition of the road surface obtained by the road surface condition estimation means 25.

The above vehicle control apparatus 57 controls the air pressure of the tire based on the above estimated condition of the road surface and shortens the braking distance on a slippery road. For example, by reducing the air pressure of the tire on a low-μ road such as an iced road, the braking distance on the low-μ road can be shortened.

That is, when the road is estimated as a low-μ road, the air pressure of the tire is automatically or manually reduced by the vehicle control means 57 to increase the ground contact area of the tire, thereby increasing friction force between the road surface and the tire to shorten the braking distance.

Any tire air pressure automatic control system is acceptable but the system comprises a pressure meter, controller, wheel with a pressure control valve, flexible joint hose, spare tank and compressor, for example.

The vehicle control apparatus 50 may be provided with means of warning the driver or passenger of a risk according to the condition of the road surface as described above to control the running state and give a warning at the same time.

EXAMPLE

A braking test was conducted on a dry asphalt road and an iced road using a test vehicle which was loaded with the vehicle control apparatus 50 of this Embodiment 9 to control the air pressure of each tire in order to confirm whether the braking distance could be shortened by controlling the air pressure of the tire automatically when the vehicle was braked on the frozen road. The above vehicle control apparatus 50 was provided with a road slipperiness warning apparatus similar to those of above Embodiments 5 and 6.

It was first confirmed that when the test vehicle of the present invention was caused to enter a frozen road at a fixed speed V of 20 km/h, a warning was given and at the same time the air pressure of the tire was automatically reduced from 220 to 160 kPa. This is because when it is detected that the vehicle enters the frozen road, the computer is programmed to give an instruction to reduce the air pressure. Further, when a braking test was conducted on a dry asphalt road and a frozen road, the braking distance of a vehicle with a conventional control apparatus was 85% longer than when running on the asphalt road whereas the braking distance of the test vehicle of the present invention was 59% longer. That is, the braking distance of the present invention can be shortened by about 14% on the asphalt road and about 30% on the frozen road. It was confirmed from this result that the vehicle can stop safely even on a frozen road by using the vehicle control apparatus 50 of this Embodiment 9.

In the above Embodiment 9, vehicle control means for controlling the locked state of each wheel and the air pressure of each tire based on the estimated condition of a road surface is provided to control the braking distance on a low-μ road. The braking distance on a low-μ road can also be shortened by performing the attitude control of a vehicle by controlling the brake unit of each wheel independently.

Alternatively, vehicle control means for controlling the attitude of a vehicle may be provided to carry out the attitude control of the vehicle, for example, by controlling the brake unit of each wheel independently based on the estimated condition of a road surface, thereby making it possible to reduce the braking distance on a low-μ road.

Further, vehicle control means for controlling the idling state of each wheel may be provided to control the idling state of the wheel by controlling the brake unit or engine speed based on the estimated condition of a road surface, thereby making it possible to reduce the braking distance on a low-μ road.

Further, in a vehicle with an automatic driving system, vehicle control means for controlling to change the inter-vehicle distance set value may be provided to change the above inter-vehicle distance set value based on the estimated condition of a road surface so as to control the inter-vehicle distance to an appropriate value, thereby making it possible to keep a safe inter-vehicle distance even on a low-μ road without fail.

In the above example, the running state of a vehicle is controlled based on the condition of a road surface estimated from a vibration transmission level like Embodiment 4. Like Embodiments 1 to 3, the running state of a vehicle may be controlled based on the condition of a road surface estimated from a vibration level.

Alternatively, the running state of a vehicle may be controlled based on the running state of each tire estimated by the tire running state estimation means 18 or 28 shown in Embodiment 6 or 7.

As having been described above, according to the present invention, the vibration level of the portion below the spring of a running vehicle or the vibration transmission level between at least two points of the portion below the spring of a vehicle is detected to estimate the condition of a road surface on which the vehicle is running. Therefore, even when the road is rough, which has been difficult with the prior art, or when the slip angle is null, the condition of the road surface can be estimated accurately. Using the estimated condition of the road surface, the risk of the condition of the road surface is warned to the passengers or the feedback control of the running state of the vehicle can be performed, thereby making it possible to greatly improve the safety of the vehicle.

Further, the condition of a road surface or the air pressure of each tire is detected from a vibration level at a plurality of frequency bands of the vibration level to detect the condition of the road surface or the running state of the tire including the existence of abnormality of the tire. Therefore, a multi-function sensing system which can accurately detect the condition of a road surface, tire pressure and further the existence of tire abnormality with one sensor, has a simple structure and many functions and is inexpensive can be constructed.

In the present invention, since an apparatus for estimating the ground contact condition of each tire or the condition of a road surface and a power generating unit for generating power by the rolling of the tire and supplying power to the above apparatus are mounted to a tire wheel to control the characteristics of each tire based on the estimated running state of the vehicle, the ground contact state of the tire can be estimated and controlled stably for a long time without changing the structure of the vehicle body.

Further, since the above power generating unit comprises a rotor magnetized and rotated by the rolling of the tire, a stator made from a high magnetic permeability material and adjacent to the rotor, a power generating coil installed within a magnetic circuit including the above rotor and stator and a capacitor for accumulating electromotive force generated in this power generating coil, power supply is made possible by energy obtained from the rolling of the tire semi-permanently and its functions can be retained stably for a long time.

What is claimed is:
1. A vehicle running state estimation method comprising:
    detecting a vibration level of a portion below a spring of a running vehicle; and
    estimating the running state of the vehicle by determining at least one of a condition of a road surface on which the vehicle is running and a running state of each tire,
        wherein said determining is based on the detected vibration level, and wherein a waveform of time changes in the vibration level is detected and the condition of the road surface on which the vehicle is running is esti- mated from a vibration level at a predetermined position of the waveform or for a predetermined time range.

2. A vehicle running state estimation method comprising: detecting a vibration level of a portion below a spring of a running vehicle; a frequency of the detected vibration level is analyzed to calculate a vibration level at a predetermined frequency band and a condition of the road surface on which the vehicle is running is estimated by comparing the calculated vibration level with a master curve which is a vibration level detected through running on a road having a predetermined condition of a road surface of the running vehicle.

3. The vehicle running state estimation method according to claim 2, wherein the master curve is prepared based on the vibration level detected at the time when the vehicle is running on a surface of a road with a usual dry asphalt pavement.

4. A vehicle running state estimation method comprising; detecting a vibration level of a portion below a spring of a running vehicle; and
estimating the running state of the vehicle by determining a degree of slipperiness of a road surface on which the vehicle is running and a running state of each tire,
wherein said determining is based on the detected vibration level, and
wherein the frequency of the detected vibration level is analyzed, at least two vibration levels at different frequency bands are calculated, an operation is carried out on the at least two calculated vibration levels, and the degree of slipperiness of the road surface is estimated from computed value.

5. A vehicle running state estimation method comprising: detecting a vibration level of a portion below a spring of a running vehicle; and
estimating the running state of the vehicle by determining a condition of a road surface on which the vehicle is running and a running state of each tire,
wherein said determining is based on the detected vibration level, and,
wherein vibration levels of at least two points of a portion below the spring with a buffer member interposed therebetween are detected to calculate a vibration transmission level of the portion below the spring between the two points at a predetermined frequency band; and the condition of the road surface is estimated from the calculated vibration transmission level.

6. A vehicle running state estimation apparatus comprising:
means of detecting a vibration level of a portion below a spring of a running vehicle;
means of calculating a vibration level at a predetermined frequency band by analyzing frequency of the detected vibration level; and
road surface condition estimation means for estimating a condition of the road surface on which the vehicle is running by comparing the calculated vibration level with the master curve which is the vibration level detected through running on a road having a predetermined road surface condition,
wherein the running state of the vehicle is estimated based on the condition of the road surface from the road surface condition estimation means.

7. The vehicle state estimation apparatus according to claim 6, wherein the master curve is prepared based on the vibration level detected through the running on the surface of a usual road with dry asphalt pavement.

8. A vehicle running state estimation apparatus comprising:
means of detecting a vibration level of a portion below a spring of a running vehicle; and
road surface condition estimation means for estimating a degree of slipperiness of a road surface from a value obtained by carrying out an operation on at least two vibration levels at different frequency bands by analyzing the frequency of the detected vibration level,
wherein the running state of the vehicle is estimated based on the degree of slipperiness of the road surface received from the road surface condition estimation means.

9. A vehicle running state estimation apparatus for estimating a running state of a vehicle based on a condition of a road surface comprising:
means of detecting vibration levels of at least two points on a portion below a spring of the running vehicle with a buffer member being interposed therebetween;
means of calculating a vibration transmission level at a predetermined frequency band between said at least two vibration detection points; and
road surface condition estimation means for estimating a condition of the road surface on which the vehicle is running from the calculated vibration transmission level.

10. A vehicle running state estimation apparatus comprising:
means of detecting a vibration level of a portion below a spring of a running vehicle;
means of calculating a vibration level at a predetermined frequency band by analyzing frequency of the detected vibration level; and
road surface condition estimation means for estimating a degree of slipperiness of the road surface on which the vehicle is running from the calculated vibration level,
wherein the running state of the vehicle is estimated based on the degree of slipperiness of the road surface received from the road surface condition estimation means, and
wherein a road surface friction coefficient μ at a time of running the vehicle is estimated based on a relationship between a surface friction coefficient μ obtained from braking distances of the vehicle under various road conditions at different speeds and at least one of the calculated vibration level at said predetermined frequency band and a calculated vibration transmission level.

11. A vehicle running state estimation apparatus comprising;
means of detecting a vibration level of a portion below a spring of a running vehicle;
means of calculating a vibration level at a predetermined frequency band by analyzing frequency of the detected vibration level; and
road surface condition estimation means for estimating a degree of slipperiness of the road surface on which the vehicle is running from the calculated vibration level,
wherein the running state of the vehicle is estimated based on the degree of slipperiness of the road surface received from the road surface condition estimation means, and
wherein the frequency band is a band including frequency of natural vibration of a tire tread land portion.

12. A vehicle running state estimation apparatus comprising:

means of detecting a vibration level of a portion below a spring of a running vehicle;

means of calculating a vibration level at a predetermined frequency band by analyzing frequency of the detected vibration level; and road surface condition estimation means for estimating a degree of slipperiness of the road surface on which the vehicle is running from the calculated vibration level, wherein the running state of the vehicle is estimated based on the degree of slipperiness of the road surface received from the road surface condition estimation means, and wherein a threshold value is set for the vibration level, and the surface of the road is estimated to be in a low friction condition when the calculated vibration level exceeds the threshold value.

13. The vehicle running state estimation apparatus according to claim 12, wherein the threshold value can be changed.

14. A vehicle running state estimation apparatus for estimating running state of a vehicle based on road surface conditions, the estimation apparatus comprising:

means of detecting a vibration level of a portion below a spring of a running vehicle;

means of computing waveform of time changes in the vibration level; and road surface condition estimation means for estimating a condition of a road surface on which the vehicle is running from the vibration level at a predetermined position of the waveform or for a predetermined time range.

15. The vehicle running state estimation apparatus according to claim 14 further comprising means of calculating the vibration level of at least one of a tire leading edge portion, tire ground contact portion and tire trailing edge portion of the waveform.

16. The vehicle running state estimation apparatus according to claim 14 which further comprises a vehicle speed detection means to estimate the condition of a road surface based on vehicle speed.

17. The vehicle running state estimation apparatus of claim 14, further comprising:

means of judging slipperiness of the road surface based on the condition of the road surface estimated by the road surface condition estimation means; and warning means for giving a warning when it is judged that the condition of the road surface is slippery.

18. The vehicle running state estimation apparatus according to claim 17, further comprising:

vehicle speed detection means to change decision on the slipperiness of the road surface and warning level based on vehicle speed.

19. The vehicle running state estimation apparatus according to claim 14, further comprising a transmitter for transmitting output of the vibration detection means for calculating a time change in the vibration level or a vibration level at a predetermined frequency band.

20. The vehicle running state estimation apparatus according to claim 14 further comprising a power generating unit mounted on a tire wheel, wherein the power generating unit generates power by rolling of each tire and supplies power for at least one of driving the vibration detection means and amplifying output of the vibration detection means.

21. A vehicle control apparatus comprising vehicle control means for controlling the running state of a vehicle based on the condition of the road surface estimated by the vehicle running state estimation apparatus of claim 14.

22. The vehicle control apparatus according to claim 21 which comprises vehicle speed detection means to control the running state of the vehicle based on vehicle speed.

23. The vehicle control apparatus according to claim 21, wherein the vehicle control means controls locked state of each wheel.

24. The vehicle control apparatus according to claim 21, wherein the vehicle control means controls attitude of the vehicle.

25. The vehicle control apparatus according to claim 21, wherein the vehicle control means controls air pressure of each tire.

26. The vehicle control apparatus according to claim 21, wherein the vehicle control means controls idling state of each wheel.

27. The vehicle control apparatus according to claim 21, wherein the vehicle control means changes inter-vehicle distance set value of an automatic driving system.

28. A tire wheel comprising: the vehicle running state estimation apparatus for estimating a running state of the vehicle by detecting the vibration level of the portion below the spring as set forth in claim 14, and a power generating unit for generating power by a rolling of each tire and supplying power to the estimation apparatus.

29. The tire wheel according to claim 28, wherein the vehicle running state estimation apparatus is mounted to the tire wheel.

30. The tire wheel according to claim 28, wherein the power generating unit comprises a rotor magnetized and rotated by the rolling of each tire, a stator made from a high magnetic permeability material and adjacent to the rotor and a power generating coil installed within a magnetic circuit including the rotor and the stator.

31. The tire wheel according to claim 30, wherein the power generating unit comprises means of accumulating electromotive force generated in the power generating coil.

32. The tire wheel according to claim 30, wherein the rotor is turned by rotating an unbalance weight the gravity center of the rotary cone of which is eccentric to a rotary shaft by the rolling of each tire.

33. The tire wheel according to claim 30, wherein an air stream generated by the rolling of each tire is introduced into the power generating unit and the rotor is turned by the introduced air stream.

* * * * *